United States Patent
Naisby et al.

(10) Patent No.: US 8,877,320 B2
(45) Date of Patent: Nov. 4, 2014

(54) MICROFLUIDIC DEVICES AND METHODS OF MANUFACTURE THEREOF

(75) Inventors: Andrew John Naisby, Salzburg (AT); Miguel Angel Torello Arevalo, Salzburg (AT); Josef Kugler, Salzburg (AT); Wolfgang Franz Reiter, Salzburg (AT)

(73) Assignee: Sony DADC Austria AG, Salzburg (AT)

( * ) Notice: Subject to any disclaimer, the term of this patent is extended or adjusted under 35 U.S.C. 154(b) by 2 days.

(21) Appl. No.: 13/399,593

(22) Filed: Feb. 17, 2012

(65) Prior Publication Data

US 2012/0213975 A1     Aug. 23, 2012

(30) Foreign Application Priority Data

Feb. 21, 2011   (GB) .................................. 1102969.1

(51) Int. Cl.
- *B32B 3/08* (2006.01)
- *B81B 1/00* (2006.01)
- *B05D 5/12* (2006.01)
- *H03L 7/23* (2006.01)
- *B01L 3/00* (2006.01)

(52) U.S. Cl.
CPC ........... *H03L 7/23* (2013.01); *B01L 2300/0645* (2013.01); *B01L 3/502707* (2013.01); *B01L 2300/0816* (2013.01)
USPC ........... 428/161; 428/164; 428/165; 428/172; 428/173; 422/50; 422/129; 422/240; 422/603; 427/123; 427/125; 427/214; 427/220; 427/404

(58) Field of Classification Search
USPC ......... 428/161, 164, 165, 172, 173, 459, 500, 428/474.4; 422/50, 129, 130, 131, 198, 422/199, 240, 603; 204/600, 601; 436/150, 436/180, 806; 427/123, 125, 214, 220, 404
See application file for complete search history.

(56) References Cited

U.S. PATENT DOCUMENTS

| | | | |
|---|---|---|---|
| 4,542,059 A * | 9/1985 | Toganoh et al. ........... | 428/32.31 |
| 5,429,735 A | 7/1995 | Johnson et al. | |
| 6,599,408 B1 | 7/2003 | Chan et al. | |
| 6,686,314 B2 * | 2/2004 | Xu et al. ........................ | 503/227 |
| 2005/0036020 A1 | 2/2005 | Li et al. | |

(Continued)

FOREIGN PATENT DOCUMENTS

| EP | 1 642 945 A1 | 4/2006 |
|---|---|---|
| JP | 2010-90211 | 4/2010 |

(Continued)

OTHER PUBLICATIONS

United Kingdom Search Report issued on Jun. 30, 2011 in corresponding United Kingdom Application No. GB1102969.1 filed on Feb. 21, 2011.

(Continued)

*Primary Examiner* — Aaron Austin
*Assistant Examiner* — Joanna Pleszczynska
(74) *Attorney, Agent, or Firm* — Oblon, Spivak, McClelland, Maier & Neustadt, L.L.P.

(57) ABSTRACT

A microfluidic device comprising: a substrate having a microfluidic channel, an electrically conductive feature comprising an electrically conductive layer arranged on a primer layer and positioned with reference to the microfluidic channel, wherein the primer layer comprises: (i) an organic polymer selected from the group consisting of: (a) a homopolymer or copolymer including a vinyl lactam repeating unit, (b) a cellulose ether; (c) polyvinyl alcohol; and (d) unmodified or modified gelatin; and (ii) a porous particulate material, the organic polymer being dispersed in the porous particulate material, is provided. Methods for manufacturing the microfluidic devices and their use in a number of applications are also provided.

15 Claims, 7 Drawing Sheets

(56) References Cited

U.S. PATENT DOCUMENTS

| | | |
|---|---|---|
| 2006/0065897 A1 | 3/2006 | Hirai et al. |
| 2007/0105972 A1 | 5/2007 | Doyle et al. |
| 2008/0079780 A1 | 4/2008 | Xiao |
| 2008/0308641 A1 | 12/2008 | Finn |
| 2009/0068383 A1* | 3/2009 | Hann et al. .................. 428/32.51 |
| 2009/0078915 A1 | 3/2009 | Lee et al. |
| 2010/0072578 A1 | 3/2010 | Kunishima |
| 2010/0209318 A1* | 8/2010 | Grande et al. ................ 422/240 |

FOREIGN PATENT DOCUMENTS

| | | |
|---|---|---|
| JP | 2010-090211 | 4/2010 |
| WO | WO 2004/068389 A2 | 8/2004 |
| WO | WO 2007/081385 A2 | 7/2007 |
| WO | WO 2008/065965 A1 | 6/2008 |
| WO | WO 2011/036509 A1 | 3/2011 |

OTHER PUBLICATIONS

Thomas I. Wallow et al., "Low-distortion, high-strength bonding of thermoplastic microfluidic devices employing case-II diffusion-meditated permeant activation", The Royal Society of Chemistry 2007, Lab Chip, 2007, vol. 7, pp. 1825-1831.

* cited by examiner

MICROFLUIDIC DEVICES AND METHODS OF MANUFACTURE THEREOF

FIELD OF THE INVENTION

This invention relates to microfluidic devices having electrically conductive features and methods of manufacturing thereof.

BACKGROUND TO THE INVENTION

Microfluidic devices are useful tools for the analysis of a variety of fluids, including chemical and biological fluids These devices are primarily composed of fluid transport channels—for example input and output channels, plus structured areas for sample diagnosis For effective processing of the fluid by the device, the fluid controllably passes through these channels Various types of microfluidic devices are known The channel cross-section dimensions in a microfluidic device can vary widely, but may be anything from the millimetre scale to the nanometre scale Reference to microfluidics in this document is not restricted to micrometre scale devices, but includes both larger (millimetre) and smaller (nanometre) scale devices as is usual in the art A basic form of a microfluidic device is based on continuous flow of the relevant fluids through the channels A development of this basic form has the active fluid conveyed through the channels in droplets held in suspension by a functionally inert carrier liquid. Generally, the bulk of the devices described herein are digital, i.e droplet-based, microfluidic devices. In such devices, a droplet is formed of a first liquid, the droplet liquid, suspended immiscibly in a second liquid, the carrier liquid The droplet liquid and the carrier liquid should be selected to be immiscible over the relevant time scale needed for good functioning of the device as determined by factors such as transit time, storage time, and reaction time within the device Droplets are generally spherical, but in use the droplets may be distorted by forces or constrained by boundaries of the channel or other parts of the microstructured device, so other shapes may exist. A droplet in the context of a digital microfluidic device is therefore a contiguous volume of a fluid held in a carrier liquid, wherein the fluid and the carrier liquid are immiscible Microfluidic devices may be made from a variety of substrate materials, including thermoplastic, glass and crystal In thermoplastic microfluidic devices, the channels can be formed by a variety of means, including injection moulding Many of the functions in known microfluidic devices are controlled electronically via electrodes arranged in or adjacent to the flow channels These electrodes may be driven by an alternating current (AC) or a direct current (DC) as required.

The electrodes may be formed by known methods such as the above-mentioned positive pressure injection or by ink jet printing. The technique comprises the printing of the pattern using a conductive ink comprising conductive particles dispersed in a solvent, followed by a sintering or curing process to dry the ink by evaporating the solvent and fusing the conductive particles to form a non-disrupted metallic conductive pathway.

WO2007/081385A2 discloses various droplet-based microfluidic devices in which electrodes for performing electrical functions on fluids are located in channels adjacent to the flow channels. To form the electrodes, the channels are filled with a molten metal alloy This can be performed with positive pressure injection with a syringe to inject the molten metal alloy into the channels The metal alloy then cools and solidifies It is also disclosed that microscopic solder spheres or ultra-violet (UV) curable conductive ink can be used to form a barrier between the flow channel and the electrode channel in order to define the geometry of the metal alloy components. The prior art document also envisages forming the electrodes by lithographic patterning using indium tin oxide (ITO) or a metal such as platinum. The microfluidic devices can include a combination of both integrated metal alloy components and a patterned electrically conductive layer. For example, it is disclosed that an electrode pair may be made from a first electrode made from a patterned electrically conductive feature and the second electrode from an electrode channel filled with a metal alloy Ink jet printing of conductive inks on thermoplastic materials is known, and is for example described in US 2009/0078915, WO 2004/068389, US 2006/0065897 and WO 2008/069565

Known ink compositions contain non-volatile solvents, particularly high boiling point polyols such as glycerol The boiling point of these polyols is typically 80 to 300° C., in some embodiments 100 to 200° C. These components act as humectants to prevent premature drying of the ink in the jetting nozzles to ensure reliability of the jetting process The sintering is normally a heating step which evaporates the solvent of the conductive ink and fuses the metal nanoparticles to form a conductive track The presence of the high boiling point liquids influences the temperature of the sintering however as any remaining organic component will impede a conductive pathway, thereby producing a product with lower and more variable conductivity. Higher sintering temperatures require a greater energy input and may damage thermoplastic substrates.

Accurate and precise placement of the actuating and sensing electrodes is critical to device performance. For example, in the case of electrodes of the type that terminate a controlled distance from the flow channel it is important to be able to define the electrode-to-flow-channel separation distance reproducibly both in terms of accuracy and precision. The separation distance may for example be in the range 10-100 micrometres It is desirable that this separation is extremely well controlled to conform to a specified distance. Moreover, it is desirable that the electrode-to-flow-channel separation can be made very small, so that the electrodes can be placed very close to the flow channel For active electrodes, i.e. those intended to be actuated with an applied voltage, closer proximity of the electrode terminating edge to the flow channel will generally allow smaller voltages to be used to achieve the same field gradient in the flow channel, i.e. the same functional effect for lower voltage. Moreover, any variance from specification in the placement position of the edges of the electrodes will lead to variance in the distance from the electrode edge to the flow channel, which in turn will lead to variance in the magnitude of the electric field that will be produced in the flow channel for a given applied voltage. Moreover, should such an electrode be mis-fabricated so that it spreads into the flow channel the device would fail, since there would be an electrical short circuit with the channel rather than the desired insulator separation provided by the thermoplastic, glass or other substrate material. Similar points will apply to the accuracy and sensitivity of electrodes arranged to form passive devices, such as inductive droplet sensors The need to accurately and precisely define the electrode positioning relative to the flow channel is a reason why it is attractive to place electrodes in their own channels as proposed in WO2007/081385A2 Nevertheless, even with this approach there is scope for lack of containment of the electrode material and the use of subsequent processing steps that will not damage or discolour a thermoplastic substrate, especially in the example where UV curable conductive ink is used

SUMMARY OF INVENTION

In one aspect, the invention provides a microfluidic device comprising.
  a substrate having a microfluidic channel;
  an electrically conductive feature comprising an electrically conductive layer arranged on a primer layer and positioned with reference to the microfluidic channel, wherein the primer layer comprises.
  (i) an organic polymer selected from the group consisting of:
    (a) a homopolymer or copolymer including a vinyl lactam repeating unit;
    (b) a cellulose ether,
    (c) polyvinyl alcohol; and
    (d) unmodified or modified gelatin;
  (ii) a porous particulate material, the organic polymer being dispersed in the porous particulate material In some embodiments, the invention provides a microfluidic device comprising:
  a substrate having a microfluidic channel,
  an electrically conductive feature comprising an electrically conductive layer arranged on a primer layer and positioned with reference to the microfluidic channel, wherein the primer layer comprises.
  (i) an organic polymer selected from the group consisting of:
    (a) a homopolymer or copolymer including a vinyl lactam repeating unit;
    (b) a cellulose ether, and
    (c) polyvinyl alcohol, and
  (ii) a porous particulate material, the organic polymer being dispersed in the porous particulate material In another aspect, the invention provides method of manufacturing a microfluidic device, the method comprising:
(A) providing a substrate having a microfluidic channel;
(B) applying a primer layer to the substrate, the primer layer comprising.
  (i) an organic polymer selected from the group consisting of:
    (a) a homopolymer or copolymer including a vinyl lactam repeating unit;
    (b) a cellulose ether, and
    (c) polyvinyl alcohol; and
  (ii) a porous particulate material, the organic polymer being dispersed in the porous particulate material;
(C) applying a conductive ink layer over the primer layer at a position referenced to the microfluidic channel, the conductive ink comprising electrically conductive particles dispersed in a humectant organic solvent In a further aspect, the invention provides a microfluidic device obtained or obtainable according to the above-mentioned method The application of the primer layer to the substrate prior to application of the conductive layer provides improved control over the physical and electrical properties of the conductive layer In particular, the following improved results are seen. The resistivity of the conductive layer is more uniform The resistivity of the conductive layer is more reproducible from device to device. Conductive layers with lower resistivity, i.e higher conductivity, can be made. The conductive layers have better controlled drying properties after deposition of the conductive ink. In particular, the spatial extent of the conductive layer is better defined both with better defined edges and also with fewer or no internal voids In addition, the primer layer absorbs the non-volatile components of the humectant organic solvents in which the electrically conductive material of the conductive ink is dispersed, so that these components are no longer present in the ink but are absorbed into the primer layer As demonstrated herein, the composition of the primer layer acts as a sieve for the undesired ingredients in the conductive ink, absorbing these components into the primer layer. This allows the final sintering step to be carried out at a lower temperature than was previously possible in the art. this is particularly desirable when the substrate is formed of a thermoplastic polymer, especially a polyolefin such as cycloolefin polymer.

BRIEF DESCRIPTION OF THE DRAWINGS

The invention is now described by way of example only with reference to the following drawings

DETAILED DESCRIPTION

Definitions

Figure 1A:
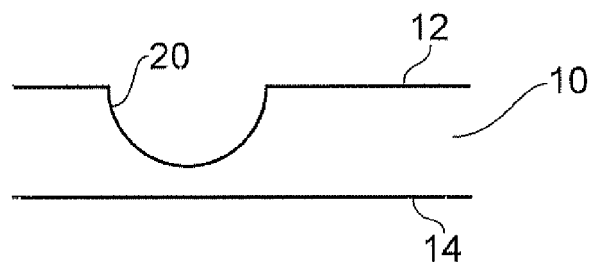
FIGS. 1A to 1F are schematic sections through a substrate showing in sequence steps in the manufacture of an electrode in a channel according to an embodiment of the invention.

In this specification "alkyl" denotes a straight- or branched-chain, saturated, aliphatic hydrocarbon radical Preferably, said "alkyl" consists of 1 to 12, typically 1 to 8, suitably 1 to 6 carbon atoms. A $C_{1-5}$ alkyl group includes methyl, ethyl, propyl, isopropyl, butyl, t-butyl, 2-butyl, pentyl, hexyl, and the like. The alkyl group may be substituted where indicated herein.

"Cycloalkyl" denotes a cyclic, saturated, aliphatic hydrocarbon radical Examples of cycloalkyl groups are moieties having 3 to 10, preferably 3 to 8 carbon atoms including cyclopropyl, cyclobutyl, cyclopentyl, cyclohexyl and cyclooctyl groups The cycloalkyl group may be substituted where indicated herein "Alkoxy" means the radical "alkyl-O—", wherein "alkyl" is as defined above, either in its broadest aspect or a preferred aspect.

"Phenyl" means the radical —$C_6H_5$ The phenyl group may be substituted where indicated herein.

"Hydroxy" means the radical —OH

"Halo" means a radical selected from fluoro, chloro, bromo, or iodo.

"Nitro" means the radical —$NO_2$.

In the devices of the present invention, an electrically conductive pattern is formed on an inert substrate having a fluidic channel.

The substrate is not particularly critical to the present invention provided it is impervious and inert to the primer layer and the conductive ink. Examples of suitable substrates include glasses and thermoplastic organic polymers.

In one embodiment, the substrate is a thermoplastic organic polymer Suitable thermoplastic organic polymers that can be used to provide the substrate include, but are not limited to, polymers formed from ethylenically unsaturated monomers, especially polyalkenes (polyolefins), polyamides (nylons), polyesters, polycarbonates, polyimides and mixtures thereof.

Examples of suitable polymers formed from ethylenically unsaturated monomers include polyolefins, which include, but are not limited to: polyethylenes, polypropylenes, poly(1-butene), poly(methyl pentene) Other examples of polymers formed from ethylenically unsaturated monomers include poly(vinyl chloride); poly(acrylonitrile); poly(tetrafluoroethylene) (PTFE—Teflon®), poly(vinyl acetate), polystyrene, poly(methyl methacrylate); ethylene-vinyl acetate copolymer; ethylene methyl acrylate copolymer, styrene-acrylonitrile copolymers; cycloolefin polymers and copolymers; and mixtures and derivatives thereof. Examples of suitable polyethylenes include, but are not limited to, low density polyethylene, linear low density polyethylene, high density polyethylene, ultra-high molecular weight polyethylene, and derivatives thereof.

Examples of suitable polyamides include nylon 6-6, nylon 6-12 and nylon 6 Examples of suitable polyesters include polyethylene terephthalate, polybutylene terephthalate, polytrimethylene terephthalate, polyethylene adipate, polycaprolactone, and polylactic acid.

In some embodiments, the thermoplastic organic polymer is a polyolefin, in particular a cycloolefin homopolymer or copolymer In this specification the term "cycloolefin homopolymer" means a polymer formed entirely from cycloalkene (cycloolefin) monomers Typically, the cycloalkene monomers from which the cycloolefin homopolymer is formed have 3 to 14, suitably 4 to 12, in some embodiments 5 to 8, ring carbon atoms Typically, the cycloalkene monomers from which the cycloolefin homopolymer is formed have 1 to 5, such as 1 to 3, suitably 1 or 2, in some embodiments 1 carbon-carbon double bonds Typically, the cycloalkene monomers from which the cycloolefin homopolymer is formed have 1 to 5, such as 1 to 3, suitably 1 or 2, in some embodiments 1 carbocyclic ring. The carbocyclic ring may be substituted with one or more, typically 1 to 3, suitably 1 or 2, in some embodiments 1 substituent, the substituent(s) being each independently selected from the group consisting of $C_{1-6}$ alkyl (typically $C_{1-4}$ alkyl, particularly methyl or ethyl), $C_{3-8}$ cycloalkyl (typically $C_{5-7}$ cycloalkyl, especially cyclopentyl or cyclohexyl), phenyl (optionally substituted by 1 to 5 substituents selected from $C_{1-6}$ alkyl, $C_{1-6}$ alkoxy, halo and nitro), or halogen The term "cycloolefin copolymer" means a polymer formed from both cycloalkene and non-cyclic alkene (olefin) monomers The monomers may be hydrocarbons or may have additional functional groups, provided they contain an ethylenically unsaturated (C=C) bond Typically, the cycloalkene monomers from which the cycloolefin copolymer is formed have 3 to 14, suitably 4 to 12, in some embodiments 5 to 8, ring carbon atoms Typically, the cycloalkene monomers from which the cycloolefin copolymer is formed have 1 to 5, such as 1 to 3, suitably 1 or 2, in some embodiments 1 carbon-carbon double bonds. Typically, the cycloalkene monomers from which the cycloolefin copolymer is formed have 1 to 3, suitably 1 or 2, in some embodiments 1 carbocyclic ring. The carbocyclic ring may be substituted with one or more, typically 1 to 3, suitably 1 or 2, in some embodiments 1 substituent, the substituent(s) being each independently selected from the group consisting of $C_{1-6}$ alkyl (typically $C_{1-4}$ alkyl, particularly methyl or ethyl), $C_{3-8}$ cycloalkyl, (typically $C_{5-7}$ cycloalkyl, especially cyclopentyl or cyclohexyl), phenyl (optionally substituted by 1 to 5 substituents selected from $C_{1-6}$ alkyl, $C_{1-6}$ alkoxy, halo and nitro), or halogen. Examples of the non-cyclic alkene copolymerised with the cycloolefin include ethylene, propylene; 1-butene, 2-methylpentene, vinyl chloride; acrylonitrile; tetrafluoroethylene; vinyl acetate; styrene; methyl methacrylate and methyl acrylate, in some embodiments ethylene or propylene, particularly ethylene Examples of commercially available cycloolefin homopolymers and copolymers usable in the present invention are those based on 8,8,10-trinorborn-2-ene (norbornene; bicyclo[2.2.1]hept-2-ene) or 1,2,3,4,4a,5,8,8a-octahydro-1,4:5,8-dimethanonapthalene (tetracyclododecene) as monomers As described in Shin et al., *Pure Appl. Chem.*, 2005, 77(5), 801-814, homopolymers of these monomers can be formed by a ring opening metathesis polymerisation: copolymers are formed by chain copolymerisation of the aforementioned monomers with ethylene Therefore, in one embodiment, the cycloolefin polymer is a cycloolefin homopolymer of general formula (A).

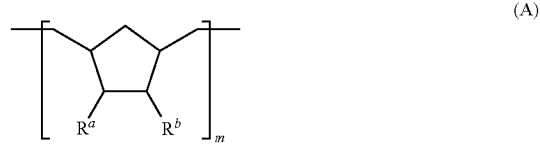

(A)

wherein.

m is such that the average molecular weight ($M_w$) of the polymer ranges from 25,000 to 250,000; and $R^a$ and $R^b$ are each independently selected from the group consisting of: hydrogen;

C$_{1-6}$ alkyl (the alkyl group being optionally substituted by 1 to 3 substituents independently selected from C$_{3-8}$ cycloalkyl, C$_{1-6}$ alkoxy, hydroxy, halo, —NH$_2$, —NH(C$_{1-6}$ alkyl), —N(C$_{1-6}$ alkyl)$_2$, —C(=O)OH or —C(=O)C$_{1-6}$ alkyl);

C$_{3-8}$ cycloalkyl (the cycloalkyl group being optionally substituted by 1 to 3 substituents independently selected from C$_{1-6}$ alkyl, C$_{1-6}$ alkoxy, hydroxy, halo, —NH$_2$, —NH(C$_{1-6}$ alkyl), —N(C$_{1-6}$ alkyl)$_2$, —C(=O)OH or —C(=O)C$_{1-6}$ alkyl);

phenyl (optionally substituted by 1 to 5 substituents selected from C$_{3-8}$ cycloalkyl, C$_{1-6}$ alkoxy, hydroxy, halo, —NH$_2$, —NH(C$_{1-6}$ alkyl), —N(C$_{1-6}$ alkyl)$_2$, —C(=O)OH, —C(=O)C$_{1-6}$ alkyl and nitro), C$_{1-6}$ alkoxy;

hydroxy;

halo,

—NH$_2$,

—NH(C$_{1-6}$ alkyl),

—N(C$_{1-6}$ alkyl)$_2$,

—C(=O)OH, or

—C(=O)C$_{1-6}$ alkyl;

or R$^a$ and R$^b$ together with the carbon atoms to which they are attached form a carbocyclic ring having 4 to 10, suitably 5 to 8, carbon atoms in 1 to 3, suitably 1 or 2, rings, the ring carbon atoms each being optionally substituted by one or more substituents selected from the group consisting of:

C$_{1-6}$ alkyl (the alkyl group being optionally substituted by 1 to 3 substituents independently selected from C$_{3-8}$ cycloalkyl, C$_{1-6}$ alkoxy, hydroxy, halo, —NH$_2$, —NH(C$_{1-6}$ alkyl), —N(C$_{1-6}$ alkyl)$_2$, —C(=O)OH or —C(=O)C$_{1-6}$ alkyl), C$_{3-8}$ cycloalkyl (the cycloalkyl group being optionally substituted by 1 to 3 substituents independently selected from C$_{1-6}$ alkyl, C$_{1-6}$ alkoxy, hydroxy, halo, —NH$_2$, —NH(C$_{1-6}$ alkyl), —N(C$_{1-6}$ alkyl)$_2$, —C(=O)OH or —C(=O)C$_{1-6}$ alkyl), phenyl (optionally substituted by 1 to 5 substituents selected from C$_{3-8}$ cycloalkyl, C$_{1-6}$ alkoxy, hydroxy, halo, —NH$_2$, —NH(C$_{1-6}$ alkyl), —N(C$_{1-6}$ alkyl)$_2$, —C(=O)OH, —C(=O)C$_{1-6}$ alkyl and nitro), C$_{1-6}$ alkoxy, hydroxy, halo,

—NH$_2$,

NH(C$_{1-6}$ alkyl),

—N(C$_{1-6}$ alkyl)$_2$,

—C(=O)OH or

—C(=O)C$_{1-6}$ alkyl

In one embodiment, R$^a$ and R$^b$ are each independently selected from the group consisting of hydrogen, C$_{1-6}$ alkyl, C$_{3-8}$ cycloalkyl or phenyl In one embodiment, R$^a$ and R$^b$ are each independently selected from the group consisting of hydrogen or C$_{1-6}$ alkyl In one embodiment, R$^a$ and R$^b$ are both hydrogen In an alternative embodiment, R$^a$ and R$^b$ together with the carbon atoms to which they are attached form a ring selected from cyclopentane, cyclohexane, cycloheptane, cyclooctane, bicyclo[2.2.1]heptane or bicyclo[2.2.2]octane, the ring carbon atoms each being optionally substituted by one or more substituents selected from the group consisting of C$_{1-6}$ alkyl (the alkyl group being optionally substituted by 1 to 3 substituents independently selected from C$_{3-8}$ cycloalkyl, C$_{1-6}$ alkoxy, hydroxy, halo, —NH$_2$, —NH(C$_{1-6}$ alkyl), —N(C$_{1-6}$ alkyl)$_2$, —C(=O)OH or —C(=O)C$_{1-6}$ alkyl), C$_{3-8}$ cycloalkyl (the cycloalkyl group being optionally substituted by 1 to 3 substituents independently selected from C$_{1-6}$ alkyl, C$_{1-6}$ alkoxy, hydroxy, halo, —NH$_2$, —NH(C$_{1-6}$ alkyl), —N(C$_{1-6}$ alkyl)$_2$, —C(=O)OH or —C(=O)C$_{1-6}$ alkyl), phenyl (optionally substituted by 1 to 5 substituents selected from C$_{3-8}$ cycloalkyl, C$_{1-6}$ alkoxy, hydroxy, halo, —NH$_2$, —NH(C$_{1-6}$ alkyl), —N(C$_{1-6}$ alkyl)$_2$, —C(=O)OH, —C(=O)C$_{1-6}$ alkyl and nitro), C$_{1-6}$ alkoxy, hydroxy, halo, —NH$_2$, —NH(C$_{1-6}$ alkyl), —N(C$_{1-6}$ alkyl)$_2$, —C(=O)OH or —C(=O) C$_{1-6}$ alkyl In this embodiment, suitably R$^a$ and R$^b$ together with the carbon atoms to which they are attached form a ring selected from cyclopentane, cyclohexane, cycloheptane, cyclooctane, bicyclo[2 2 1]heptane or bicyclo[2.2.2]octane, the ring carbon atoms each being optionally substituted by one or more substituents selected from the group consisting of C$_{1-6}$ alkyl, C$_{3-8}$ cycloalkyl or phenyl.

In some embodiments, m is such that the average molecular weight (Mw) of the polymer ranges from 50,000 to 150,000

In another embodiment, the cycloolefin polymer is a cycloolefin polymer of formula (B).

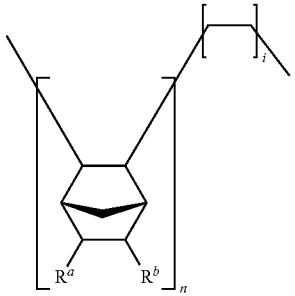

(B)

wherein.

n and l are such that the average molecular weight (M$_w$) of the polymer ranges from 25,000 to 250,000;

n is such that the mole fraction of cycloolefin repeating units ranges from 0 2 to 0 7;

l is such that the mole fraction of ethylene repeating units ranges from 0.8 to 0 3; and R$^a$ and R$^b$ are as defined above for formula (A), either in its broadest aspect or a preferred aspect Chemical structures of the repeating units of certain specific cycloolefin homopolymers useful in the present invention are shown below

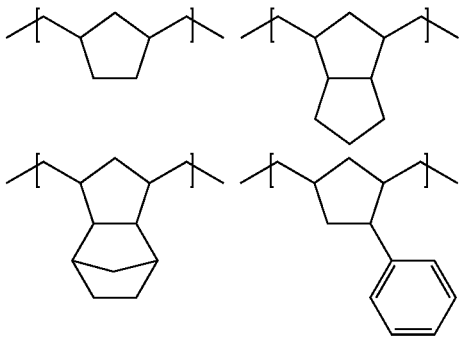

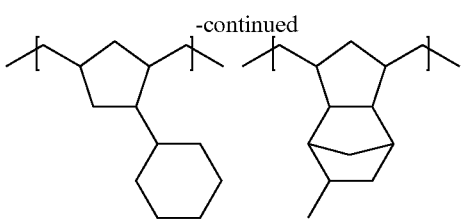

An example of a ring opening metathesis polymerisation scheme for norbornene derivatives, as well as a scheme for their copolymerisation with ethene is shown below

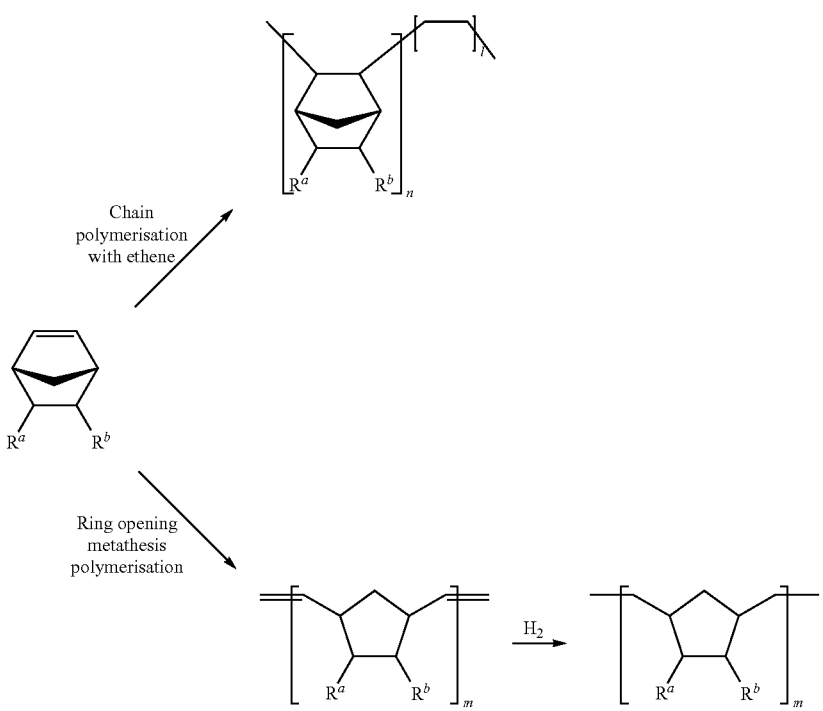

In the above reaction scheme, l, m, n, $R^a$ and $R^b$ are as defined above, either in its broadest aspect or a preferred aspect.

In some embodiments, n and l are such that the average molecular weight ($M_w$) of the polymer ranges from 50,000 to 150,000

In some embodiments, n is such that the mole fraction of cycloolefin repeating units ranges from 0.3 to 0.6; and l is such that the mole fraction of ethylene repeating units ranges from 0.7 to 0.4

Another class of materials known to be suitable for microfluidic device substrates is the class of silicone polymers polydimethylsiloxane (PDMS). These polymers have the general formula:

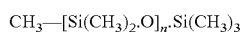

where n is the number of repeating monomer [SiO(CH$_3$)$_2$] units.

In the above formula, n is such that the average molecular weight (Mw) of the polymer ranges from 100 to 100,000, in some embodiments 100 to 50,000

Examples of suitable glasses that can be used to provide the substrate include silica glasses, in particular phosphosilicate glass compounds and borosilicate glass compounds Crystal substrates, in particular semiconductor substrates, such as silicon substrates, may also be used. Another suitable crystal for the substrate is lithium niobate.

The device has a primer layer applied to the substrate The primer layer is capable of absorbing the humectant organic solvent (particularly although not exclusively the higher boiling point components thereof) in which the metal particles of the conductive ink are dissolved This allows the subsequent sintering to be carried out at a much lower temperature than was previously possible in the art. this is particularly advantageous for thermoplastic substrates as it avoids overheating and possible damage to the substrate The primer layer comprises of a porous particulate material dispersed in an organic polymer The organic polymer acts as a binder for the porous particulate material and has a high cohesive strength The organic polymer contains hydrophilic functional groups (such as hydroxyl, amino, carbonyl, carboxyl, carboxylic ester, sulfone, sulfonic acid) capable of bonding to the hydrophilic functional groups (especially the hydroxyl groups) in the organic solvent Such groups therefore enable the polymer to bind the molecules of the humectant organic solvent. In some embodiments, the polymer also has at least partial solubility in the humectant organic solvent of the conductive ink—this further serves to absorb the less volatile components present in the ink, hence leaving a purer electrically conductive layer on the surface of the primer after printing.

In some embodiments, the primer layer contains up to 30%, in some embodiments up to 25%, in some embodiments up to 20%, in some embodiments up to 15%, and in some embodiments up to 10% of the organic polymer (as a percentage by weight of the concentrated primer, before dissolution in solvent(s)).

In one embodiment, the organic polymer is a polymer including a vinyl lactam repeating unit (also referred to herein as a "vinyl lactam polymer"), i.e a polymer including a repeating unit of the following general formula (I):

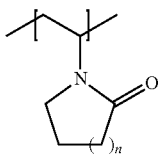

(I)

wherein n is 0 to 6

In some embodiments n is 1, 2 or 3, in some embodiments 1 or 3, in some embodiments 1 When n is 1, the repeating unit is a vinyl pyrrolidone repeating unit. When n is 3, the repeating unit is a vinyl caprolactam repeating unit.

The vinyl lactam polymer may be a homopolymer (i.e. where the vinyl lactam is the only repeating unit) or a copolymer including another vinyl repeating unit in addition to the vinyl lactam repeating unit. When the vinyl lactam polymer is a copolymer, the other repeating unit may be any known vinyl repeating unit; examples include. ethylene, propylene; 1-butene, 2-methylpentene; acrylonitrile; vinyl acetate, styrene, methyl methacrylate, methyl acrylate; an alkylaminomethacrylate; an alkylaminomethacrylamide, and mixtures thereof. The vinyl repeating units all have carbon-carbon double bonds in their monomeric form; these are broken to bond together the repeating units of the polymer in which the carbon atoms are singly bonded.

When the organic polymer is a copolymer containing a vinyl lactam repeating unit, the copolymer typically contains at least 30%, in some embodiments at least 40%, vinyl lactam repeating units (as a percentage of the total number of repeating units in the copolymer)

Examples of copolymer types include: alternating copolymers (where the repeating A and B units alternate A-B-A-B-A-B); block copolymers which comprise two or more homopolymer subunits linked by covalent bonds (AAAAAAAA-BBBBBBBB-AAAAAAA-BBBBBBB) and random copolymers where the repeating A and B units are distributed randomly. In some embodiments, the copolymers used in the present invention are random copolymers.

In some embodiments, the organic polymer is a homopolymer or copolymer of vinyl pyrrolidone In one embodiment, the organic polymer is polyvinyl pyrrolidone (ie a homopolymer wherein vinyl pyrrolidone is the only repeating unit) In another embodiment, the organic polymer is a copolymer including another vinyl repeating unit, examples include ethylene, propylene, 1-butene, 2-methylpentene, acrylonitrile, vinyl acetate; styrene, methyl methacrylate, methyl acrylate; an alkylaminomethacrylate, an alkylaminomethacrylamide; and mixtures thereof.

When the organic polymer is a copolymer containing a vinyl pyrrolidone repeating unit, the copolymer typically contains at least 30%, in some embodiments at least 40%, vinyl pyrrolidone repeating units (as a percentage of the total number of repeating units in the copolymer).

In one embodiment, the organic polymer is a copolymer including an acrylic or methacrylic repeating unit in addition to the vinyl lactam (in some embodiments vinyl pyrrolidone) repeating unit. In this specification the terms "acrylic repeating unit" or "methacrylic repeating unit" mean the repeating unit of general formula (II):

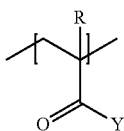

(II)

wherein R is H or methyl, and

Y is. $OR^1$ or $NR^1R^1$ wherein each $R^1$ is H or $C_{1-6}$ alkyl (optionally substituted with one or more groups selected from halogen, OR' or NR'R' wherein each R' is independently hydrogen or $C_{1-6}$ alkyl).

When R is H, the repeating unit is an acrylic repeating unit. When R is methyl, the repeating unit is a methacrylic repeating unit In some embodiments, the acrylic or methacrylic repeating unit is an alkylaminomethacrylate or alkylaminomethacrylamide repeating unit Such repeating units have the general formula (III).

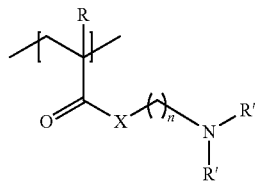

(III)

wherein:

R is hydrogen or methyl,

X is O or NR", wherein R" is hydrogen or $C_{1-6}$ alkyl, n is 1 to 10, and each R' is independently H or $C_{1-6}$ alkyl.

When X is O, the repeating unit is an alkylaminomethacrylate repeating unit When X is NR", the repeating unit is an alkylaminomethacrylamide repeating unit In this embodiment, R is methyl.

In this embodiment, n may be 1 to 4, particularly 2 or 3

In this embodiment, in some embodiments one or both groups R' are H or methyl, particularly methyl.

In a particularly preferred embodiment, the organic polymer is a copolymer of vinyl pyrrolidone and dimethylaminoethylmethacrylate. Such a copolymer is commercially available as Copolymer 955™ from ISP Corporation, New Jersey, USA. Typically, Copolymer 958 comprises 40-60% vinyl pyrrolidone repeating units and 60%-40% dimethylaminoethylmethacrylate repeating units.

In an alternative embodiment, the organic polymer may comprise a blend of polymers.

(1) a polymer containing a vinyl lactam repeating unit, as defined and exemplified above, either in its broadest aspect or a preferred aspect, and (2) an acrylic polymer In this context the term "acrylic polymer" means a polymer comprising acrylic or methacrylic repeating units (as defined and exemplified above, either in its broadest aspect or a preferred aspect). The acrylic polymer may be a homopolymer (i.e. a polymer consisting only of one type of acrylic or methacrylic repeating unit) or a copolymer (i.e. a polymer comprising one or more other repeating units in addition to the acrylic or methacrylic repeating unit, the additional repeating unit may be any of the vinyl repeating units defined and exemplified above) Suitably, the acrylic polymer is an acrylic homopolymer, especially methyl methacrylate In one embodiment, the organic polymer is a cellulose ether. In this specification "cellulose" means the polysaccharide consisting of a linear chain of about 100 to about 100,000 (in some embodiments 500 to 50,000) β(1→4) linked D-glucose units. Cellulose ethers are cellulose derivatives wherein one or more of the hydroxyl groups of the cellulose molecule are alkylated with an alkyl group (as defined and exemplified above, in some embodiments $C_{1-6}$ alkyl, in some embodiments $C_{1-4}$ alkyl), the alkyl group being optionally substituted with a group selected from $C_{1-6}$ alkoxy, hydroxyl and —$CO_2H$ or —$CO_2(C_{1-6}$ alkyl). The alkyl groups may be the same or different, a cellulose ether may have one or more different alkyl groups on the same molecule. Typical examples include methylcellulose, ethylcellulose, ethyl methyl cellulose, hydroxyethyl cellulose, hydroxypropyl cellulose, hydroxyethyl methyl cellulose, hydroxypropyl methyl cellulose (HPMC), ethyl hydroxyethyl cellulose and carboxymethyl cellulose Hydroxypropyl cellulose and hydroxypropyl methyl cellulose are preferred In one embodiment, the organic polymer is a polyvinyl alcohol. As is well known in the art, polyvinyl alcohol is prepared by first preparing a polyvinyl ester such as polyvinyl acetate followed by partial or complete hydrolysis of the ester bonds in the polyvinyl ester to leave the polymer substituted with hydroxyl groups. The degree of hydrolysis may vary from 30 molar % to 100 molar % (ie complete hydrolysis so only hydroxyl groups are present on the polymer) The molar % degree of hydrolysis of the polyvinyl alcohol may be measured using one of the following test methods. International Standards ISO 15023-1:2001, ISO 15023-2:2003 and Japanese Industrial Standard (WS) K6726

In some embodiments, the polyvinyl alcohol used in the present invention has a degree of hydrolysis of between 30 and 99 molar %: in some embodiments 35 to 95 molar %

In one embodiment, the polyvinyl alcohol used in the present invention has a degree of hydrolysis of 40 to 80 molar %, in some embodiments 50 to 70 molar %. Polyvinyl alcohols having this degree of hydrolysis have been found to absorb the humectant organic solvent in the conductive ink most effectively and be most soluble in the preferred organic solvents used for micro-dispensing a primer layer.

In one embodiment, the polyvinyl alcohol used in the present invention has a degree of hydrolysis of 75 to 95 molar %, in some embodiments 80 to 90 molar % Polyvinyl alcohols having this degree of hydrolysis have been found to confer optimum printability on the conductive ink but have limited solubility in the preferred organic used for micro dispensing a primer layer Therefore the preferred degree of hydrolysis for polyvinyl alcohol in the present invention is 70-90 molar %

As is known in the art, the degree of hydrolysis determines the degree of crystallinity of a polyvinyl alcohol polymer The degree of crystallinity may also depend on a number of factors such as stereoregularity (tacticity), degree of branching and the crystalline melting point/glass transition temperature Without wishing to be bound by current theory, it is also proposed that the degree of crystallinity of polyvinyl alcohol can vary whilst maintaining a constant degree of hydrolysis, thereby improving the polymers solubility in the organic solvents contained in the present invention. The preferred polymer exhibiting a good compromise for solubility in organic solvents used for micro-dispensing and optimum printability of a conductive ink is commercially available from Nippon Gohsei under the trade name Nichigo G-Polymer, specifically Nichigo G-Polymer OKS 8041

In one embodiment, the organic polymer used in the primer layer is unmodified or modified gelatin As is well known to those skilled in the art, gelatin comprises a mixture of polypeptides and proteins. As indicated in "The Science and Technology of gelatin", (Food Science & Technology Monographs) ed A G Ward A Courts, 13 Jun. 1977, the molecular weight of the proteins and polypeptides can vary from 30,000 to 300,000 g/mol.

Gelatin is typically produced by degradation of collagen. Collagen is a protein which may be extracted from sources such as bones, skin, connective tissues, organs and some intestines of animals such as domesticated cattle, chicken, and pigs The degradation of collagen to produce gelatin may be carried out using a number of possible reagents well known to those skilled in the art, including but not limited to acids, bases and enzymes.

As is known to those skilled in the art, gelatin is capable of modification by reaction of the free hydroxyl groups and amino groups with a suitable reagent. For example, the hydroxyl groups may be etherified by substitution of the hydrogen with an alkyl group, or esterified by substitution of the hydrogen with an acyl group, or acetalised by condensation of two hydroxyl groups with a carbonyl-containing compound Examples of suitable reagents include alkylating agents, such as alkyl halides or sulfonates, acylating agents, such as acid chlorides and acid anhydrides, and carbonyl compounds, such as, aldehydes and ketones. The reaction of gelatin with aldehydes may lead to crosslinking to cure the polymer.

Reaction with acylating agents, such as acid anhydrides, may lead to a change in the properties of the gelatin, including its chemical or thermal stability In some embodiments, the modified gelatin is an acyl-modified gelatin, especially a succinyl-modified gelatin and particularly an alkylsuccinyl-modified gelatin Examples of suitable modified gelatins are described in DE 19721238A and U.S. Pat. No. 5,439,791 A particularly preferred example is the photographic gelatin available from GELITA®.

In some embodiments, the organic polymer used in the primer layer is cross-linked. Cross-linking the primer after formation of the electrode pattern increases the dimensional and environmental stability of the final electrode pattern on the microfluidic device Examples of suitable curing agents are polyaminoamide-epichlorohydrin resins, also melamine and benzoguanamine derivatives—according to the general chemical formulae:

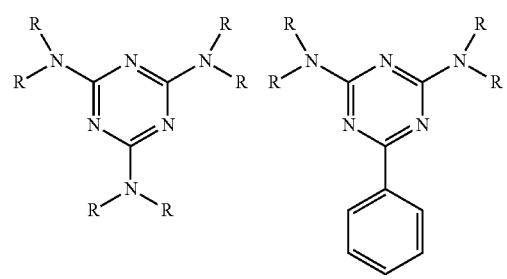

where R = H ——OCH$_3$, ——OC$_4$H$_9$ and ——CH$_2$OH

The organic polymer is typically supplied or prepared as a concentrated solution, in some embodiments in a hydrophilic solvent. Suitable hydrophilic solvents include water and oxygenated solvents, such as alcohols, ethers, ketones and esters. Preferred solvents include C$_{1-6}$ alcohols such as methanol, ethanol, propanol, isopropanol, butan-1-ol, butan-2-ol, pentan-1-ol and hexan-1-ol, of which ethanol is particularly preferred The primer layer according to the present invention also comprises of a porous particulate material. The porous particulate material acts as a filler and further aids in the absorption of the humectant organic solvents (particularly the non-volatile components thereof) contained in the conductive ink The porous particulate material also serves to regulate the flow of the primer layer when dispensed into a microfluidic channel Undesirable effects such as overflow of the primer into neighbouring regions on the fluidic device can be controlled by the appropriate choice and concentration of the porous particulate material.

In some embodiments, the porous particulate material comprises a molecular sieve In this specification the term "molecular sieve" means a material containing pores of a precise and uniform size and which are capable of acting as an adsorbent for gases and liquids Molecules small enough to pass through the pores are adsorbed while larger molecules, specifically metallic particles present in a conductive ink jet ink, are not Typically, the pore volume ranges from 0 20 to 1.20 ml/g, suitably from 0.40 to 0 60 ml/g Examples of suitable porous particulate materials include metal and semimetal oxides such as silica (especially amorphous silica), aluminas (including boehmite, aluminium oxide monohydrate and Bayerite, aluminium oxide trihydrate), titania, zeolites (porous aluminosilicate materials), barium sulphate and silica-alumina hydrates and oxides In one embodiment, the porous particulate material is alumina boehmite. Particularly suitable alumina boehmites include the range of water dispersible alumina boehmites available as DISPERAL® and DISPAL® from Sasol.

In another embodiment, the porous particulate material is silica, especially fumed silica.

In another embodiment, the porous particulate material is a zeolite. Zeolites are porous aluminosilicate materials capable of acting as molecular sieves. Zeolites have a porous structure that can accommodate a wide variety of cations, such as $Na^+$, $K^+$, $Ca^{2+}$, and $Mg^{2+}$ These positive ions can readily be exchanged for others in a contact solution Examples of suitable zeolites include amicite, analcime, barrerite, bellbergite, bikitaite, boggsite, brewsterite, chabazite, clinoptilolite, cowlesite, dachiardite, edingtonite, epistilbite, erionite, faujasite, ferrierite, garronite, gismondine, gmelinite, gobbinsite, gonnardite, goosecreekite, harmotome, herschelite, heulandite, laumontite, levyne, maricopaite, mazzite, merlinoite, mesolite, montesommaite, mordenite, natrolite, offretite, paranatrolite, paulingite, pentasil (also known as ZSM-5), perlialite, phillipsite, pollucite, scolecite, sodium dachiardite, stellerite, stilbite, tetranatrolite, thomsonite, tschernichite, wairakite, wellsite, willhendersonite and yugawaralite.

The porous particulate material is typically present as a dispersion in a solvent. Typically, the solvent is water or a hydrophilic organic solvent such as an alcohol, an ether (particularly a glycol ether such as those described and exemplified below), a ketone or an ester. In some embodiments, the solvent in which the porous particulate material is dispersed is water.

In some embodiments, the primer layer contains at least 70%, in some embodiments at least 75%, in some embodiments at least 80%, in some embodiments at least 85%, and in some embodiments at least 90% by weight of the porous particulate material (as a percentage by weight of the concentrated primer, before dissolution in the solvent)

The primer layer is generally applied to the substrate diluted in solution, in some embodiments in a hydrophilic/hydrophobic solvent The solvent used to dilute the primer layer should in some embodiments exhibit a lower surface tension with respect to surface energy of the microfluidic substrate. The surfactant-like properties of the solvent, low surface tension and slow evaporation rate enables the formulated primer layer to flow across the region of the substrate only where it is intended to be applied. Suitable solvents include oxygenated solvents, such as alcohols, and ethers (particularly glycol ethers such as those defined and exemplified below), ketones and esters.

It is preferred that the solvent in which the primer layer is diluted is a glycol ether These solvents exhibit a good range of properties such as good solvency of hydrophilic and hydrophobic coating polymers, good flow behaviour on hydrophobic surfaces and controllable evaporation (drying). Examples of suitable glycol ethers include. ethylene glycol mono($C_{1-6}$) alkyl ethers such as ethylene glycol monopropyl ether, ethylene glycol monoisopropyl ether (isopropoxyethanol) and ethylene glycol monobutyl ether, ethylene glycol phenyl ether, diethylene glycol mono($C_{1-6}$)alkyl ethers such as diethylene glycol monomethyl ether, diethylene glycol monoethyl ether (CARBITOL™), diethylene glycol monobutyl ether and diethylene glycol monohexyl ether, triethylene glycol mono ($C_{1-6}$)alkyl ethers (alkoxytriglycols) such as triethylene glycol monomethyl ether (methoxytriglycol), triethylene glycol monoethyl ether (ethoxytriglycol) and triethylene glycol monobutyl ether (butoxytriglycol); propylene glycol ($C_{1-6}$) alkyl ethers such as propylene glycol methyl ether, propylene glycol n-propyl ether, propylene glycol n-butyl ether, propylene glycol phenyl ether; dipropylene glycol ($C_{1-6}$)alkyl ethers such as dipropylene glycol methyl ether, dipropylene glycol n-propyl ether and dipropylene glycol n-butyl ether and tripropylene glycol ($C_{1-6}$)alkyl ethers such as tripropylene glycol methyl ether and tripropylene glycol n-butyl ether A particularly preferred example is ethylene glycol monoisopropyl ether (isopropoxyethanol).

In some embodiments, the primer layer is applied in a solution containing 50 to 95%, in some embodiments 60 to 90%, in some embodiments 65 to 80%, by weight of the concentrated primer layer and 5 to 50%, in some embodiments 10 to 40%, in some embodiments 20 to 35%, by weight of the diluting solvent The devices of the present invention further comprise an electrically conductive pattern over the primer layer. The conductive material is formed by applying a conductive ink, comprising particles of an electrically conductive material dispersed in a humectant organic solvent, over the primer layer and sintering the substrate to evaporate any solvent in the ink to fuse the electrically conductive particles into the conductive pattern A wide range of conductive inks are commercially available from a number of sources Examples of suitable conductive inks are those available from Sun Chemical Corporation commercially available under the trade names U5603 and U5714

In some embodiments, the electrically conductive material from which the particles are formed is a metal In an alternative embodiment, the conductive material is a conductive form of carbon. Examples of conductive forms of carbon include graphite and carbon nanotubes In a further alternative embodiment, the conductive material is a conductive metal oxide These materials are metal oxides doped with another metal in sufficient amounts to cause the material to be electrically conductive. Examples of conductive metal oxides include indium tin oxide (ITO), antimony tin oxide, indium-doped cadmium oxide and aluminium-doped zinc oxide.

When the conductive material is a metal, the metal is not particularly limited provided it does not react with the solvents. Examples of suitable metals include alkaline earth metals such as beryllium, magnesium, calcium, strontium and barium; transition metals such as zinc, molybdenum, cadmium, scandium, titanium, vanadium, chromium, manganese, iron, cobalt, nickel, copper, yttrium, zirconium, niobium, technetium, ruthenium, rhodium, palladium, silver, hafnium, tantalum, tungsten, rhenium, osmium, iridium, platinum and gold, lanthanoids such as lanthanum, cerium, praseodymium, neodymium, promethium, samarium, europium, gadolinium, terbium, dysprosium, holmium, erbium, thulium, ytterbium and lutetium; and p-block metals such as aluminium, gallium, indium, tin, thallium, lead and bismuth. Preferred metals include nickel, copper, palladium, tungsten, cadmium, silver, platinum and gold. A particularly preferred example is silver It will be understood that the alloys or mixtures of two or more of the above-mentioned metals and other conductive compounds may be used In some embodiments, the metallic or electrically conductive particles dispersed in the conductive ink are nanoparticles The particle size of the nanoparticles should be such that they are not absorbed into the primer layer. Typically, the particle size of the nanoparticles ranges from 1 to 800 nm, in some embodiments 5 to 200 nm, in some embodiments 50 to 150 nm The conductive ink may optionally further include a corrosion inhibitor Such corrosion inhibitors are required when the metal is non-noble (i e a metal other than ruthenium, rhodium, palladium, silver, osmium, iridium, platinum or gold) to prevent oxidation of the metal. Examples of corrosion inhibitors include hydrazine, amines such as hexamine, phenylenediamine or dimethylethanolamine or sterically hindered amines such as those described and exemplified below, quaternised amines, polyamines such as polyaniline; aldehydes such as cinnamaldehyde; imines; and inorganic corrosion inhibitors such as nitrites (eg sodium nitrite), chromates and phosphates; and mixtures of any thereof. In preferred embodiments, the corrosion inhibitor is a sterically hindered amine. Suitable hindered amines include diethanolamine, triethanolamine, imidazole derivatives and their salts with polycarboxylic acids Particularly suitable corrosion inhibitors are commercially available from BASF Corporation under the trade names Corrosion Inhibitor Amine O, Irgacor L184, and Irgacor L190 Plus. These are particularly suitable because of their solubility in hydrophilic formulations.

In the conductive inks used in the present invention, the metallic particles are dispersed in a humectant organic solvent The humectant organic solvent is a liquid solvent capable of absorbing water, typically by forming hydrogen bonds with molecules of water Whether a particular organic solvent is a humectant can typically be measured by allowing the solvent to stand in a humid or aqueous environment and measuring whether absorption of water by the organic solvent causes an increase in weight In some embodiments, the humectant organic solvent may be capable of absorbing 1 to 100%, typically 2 to 50%, in some embodiments 5 to 40%, by weight of water (based on the weight of the starting organic solvent)

Typically, the humectant organic solvent contains one or more (in some embodiments more than one) hydrophilic groups, such as hydroxyl, amino, carbonyl, carboxylic acid and carboxylic ester Preferred classes of humectant organic solvents include oxygenated solvents, such as alcohols (particularly polyols, ie alcohols containing more than one OH group), ethers, ketones and esters Particular examples of humectant organic solvents include polyol solvents, in particular diols having from 2 to 8, in some embodiments 2 to 4, carbon atoms such as, ethylene glycol, propylene glycol, 1,4-butanediol, 1,5-pentanediol, 1,6-hexanediol, 1,7-heptanediol, 1,8-octanediol, diethylene glycol, triethylene glycol and tetraethylene glycol, and triols having from 3 to 8 carbon atoms such as glycerol In some embodiments, the solvent may contain small amounts (typically less than 5% by weight) of a glycol ether (such as those defined and exemplified above), such as isopropoxyethanol In some embodiments, the primer layer and conductive ink is formed in a channel in the substrate to which the electrodes are applied This is a convenient way of defining the location of the electrode or other conductive feature, in particular in relation to the fluid flow channel with which it is functionally associated. In other embodiments, the primer layer and conductive ink may be applied to an unstructured surface portion of the substrate, with their location, extent and registry to other features being defined as necessary by the technique used to deposit them, e.g. printing, photolithography etc. Generally it is preferable that conductive ink will only be applied on primer When applying features to an unstructured surface, it is therefore preferable if the primer layer features extend laterally beyond the planned extent of the conductive ink layer so there is a margin for error in registry of the ink deposition to avoid ink being deposited on un-primed surface. In an extreme example, the entire surface may be primed prior to deposition of the conductive ink, for example by dipping the substrate in the primer solution, spraying the primer solution onto the substrate, by printing or other method. This may be attractive in the case that conductive features are to be applied to the back side of the substrate. By back side it is meant that there is a front side of the substrate bearing channels and a featureless, or at least channel-free, back side.

Once the conductive ink has been applied to the primer layer, the substrate is sintered to evaporate the solvent and allow the conductive particles present in the ink to fuse together to form a conductive track. Typically, the substrate is sintered at a temperature of 60 to 100° C., in some embodiments 70 to 90° C. Typically, the substrate is sintered for a time of 1 minute to 1 hour, in some embodiments 5 to 20 minutes.

Figure 1B:
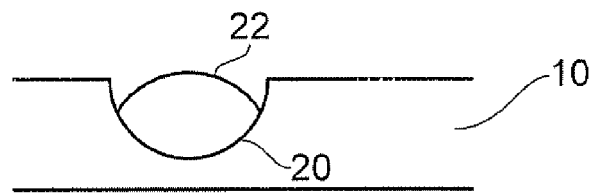

Optionally, as an alternative to a steady state sintering process as described above, i e. a bake, it is possible to use a transient process whereby energy is optically dumped into the conductive ink by applying intense illumination over the surface for a short time, for example with a xenon lamp or a UV, visible or infrared source, optionally a laser or LED source The wavelength of the light is chosen such that it has an absorption length in the conductive ink layer which is approximately equal to or less than the thickness of the conductive ink. This results in the light energy being fully, or at least mostly, absorbed in the conductive ink, thereby avoiding any substantial heating of the substrate underlying the conductive ink In this way, thermal distortion or other damage to the substrate can be avoided Method of Manufacture FIGS. 1A to 1F are schematic sections through a substrate showing in sequence steps in the manufacture of an electrode in a channel according to an embodiment of the invention. The process is typically carried out under cleanroom conditions Optionally, the substrate is cleaned with a degreasing solvent (typically an isopropanol/water mixture). The substrate may be cleaned with compressed air to remove dust or contamination FIG. 1A shows a substrate 10 having an upper or top surface 12 and a lower or bottom surface 14. The substrate 10 has a semi-circular section channel 20 formed in the upper surface 12, e.g. by moulding, stamping, machining or etching. The channel 20 is intended to define the location of an electrode, i.e. the channel is an "electrode" channel, as opposed to a flow channel, as discussed further above FIG. 1B shows the channel 20 partly filled with a solvent-containing primer solution 22 The primer solution can be applied by microdispensing into the channel, e.g. with a syringe, micropipette or ink jet print head nozzle. The composition of the primer solution allows it to be applied to the channel by capillary action, resulting in a smooth and even coverage of the channel. The primer may alternatively be dispensed by a printing or photolithography in some embodiments.

Figure 1C:
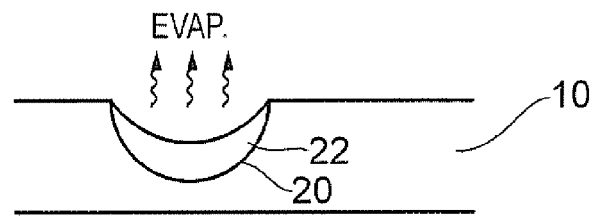

FIG. 1C schematically illustrates the primer solution during a drying phase during which the solvent evaporates. The composition of the primer layer may be selected to allow the drying to be carried out within a reasonable time at room temperature, thereby avoiding the need for heating. Alternatively, the substrate may be held at an elevated temperature to enable or at least accelerate drying.

Figure 1D:
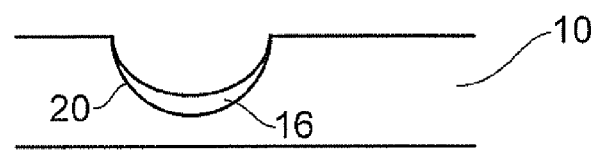
Figure 1E:
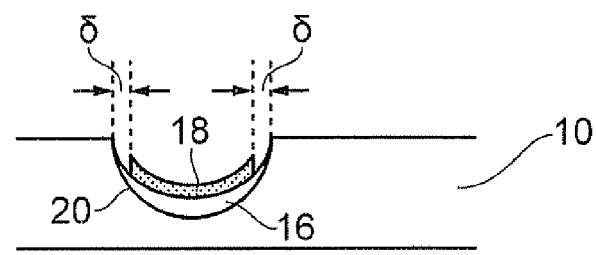

FIG. 1D schematically illustrates the component after completion of the primer drying phase A solid primer layer 16 has been formed to cover substantially the entire inner surface of the channel. The primer layer is thicker at the base of the channel than in the side walls, especially near the top of the side walls where the primer layer is significantly thinner, as schematically illustrated Depending on how the primer solution is applied, the uppermost side wall regions of the channel may not be primed FIG. 1E schematically illustrates the channel cross-section after the next step of depositing a layer of conductive ink 18 over the primer layer 16 The deposition of the conductive ink may be performed by ink jet printing, a technique well known to those skilled in the art Following application of the conductive ink layer 18, the primer layer 16 absorbs the non-volatile components of the humectant organic solvents in which the conductive material of the ink is dispersed, so that these components are no longer present in the ink. As illustrated, it may be advantageous not to print right up to the lateral edges of the channel, but rather to leave a gap δ between the edge of the printed layer and the edge or rim of the channel. The provision of such a gap reduces the risk of printing on untreated substrate in the case that a registration error occurs. The provision of such a gap also avoids excessive densities of ink being deposited near the edges of the channel where there is a steep slope of the channel side-wall.

Figure 1F:
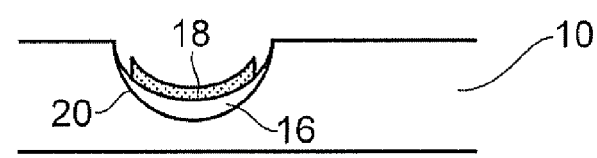

FIG. 1F schematically illustrates a sintering step in which the conductive particles present in the ink are fused together. The sintering also removes any remaining solvent in the ink 18 to produce a substrate having a conductive layer 20 over the primer layer 16 It is noted that the absorption of the non-volatile components of the humectant organic solvents by the primer layer allows the sintering step to be carried out at a lower temperature than would otherwise be possible If the curing agents are present in the primer, this can serve to harden the primer layer during the sintering step The curing agents chosen are slow to react, or self-crosslinking, to avoid any compositional change during the printing step. any hardening of the combined layers (i e the primer and conductive layer) should occur after printing.

Where the curing agent is a polyaminoamide-epichlorohydrin curing resin the hardening occurs at neutral to alkaline pH. the hardening can therefore be accelerated by organic polymers having an amine functionality, such as a vinyl pyrrolidone-dimethylaminoethylmethacrylate copolymer (Copolymer 958)

The conductive layer 20 will typically be used as an electrode layer in an active or passive device, but may also form any other feature, for example may form part of an antenna structure The shape of the channel need not be approximately semi-circular in cross-section as illustrated Other shapes may be used For example, the base and/or side walls of the channels may be flat or have flat portions. Another example is that the channels may be formed with a V-groove Moreover, the invention is relevant not only for forming conductive features to control or sense flow in channels of microfluidic devices, but also for forming conductive features in other parts of microfluidic devices, such as reaction chambers or reagent reservoirs Device Applications Some known functions in droplet-based microfluidics are to:
1. form, create or produce one or more droplets on demand
2. sort droplets from a series
3. route droplets at a junction
4. coalesce or fuse two droplets to a combined droplet, e g to initiate or terminate a reaction
5. divide or split a droplet
6. induce mixing inside a droplet
7. sense passage of a droplet, or a certain kind of droplet passing down a channel
8. analyse one or more parameters of each droplet passing a sensor
9. electrically charge a droplet, e.g. to assist its future manipulation
10. electrically neutralize (discharge) a droplet Many if not all these functions may be controlled by application or detection of electromagnetic fields, in particular electric fields, but also magnetic fields The coalescing function is important, since it is typically the basis under which the main activity of the device is performed It is typical to coalesce droplets from different streams, e.g. sample and reagent, to form a coalesced droplet in which a chemical or biological reaction takes place. Such a combined droplet is sometimes referred to in the art as a nanoreactor, not just when in the nanometre scale, but even when in the micrometre scale Actuating or sensing electrodes may be arranged in, or to extend into, the flow channels to contact the fluid, or may be arranged outside the flow channels, adjacent thereto, so there is an insulating medium, e.g the substrate material and/or air, between the electrode(s) and the droplet-containing carrier liquid The term actuating electrodes is used to refer to electrodes of an active component, whereas the term sensing electrode is used to refer to electrodes in a passive component.

For actuating electrodes, the magnitude of the electric field created in the flow channel is typically of the order of $10^6$-$10^8$ V/m.

A number of known functions induced by electric field based active components are as follows.
1. charging droplets by applying an electric field via adjacent electrodes connected to a voltage source or current source
2. dividing a droplet into two droplets by inducing a dipole moment by applying an electric field via adjacent electrodes connected to a voltage source or current source which causes oppositely charged ions to move in opposed directions and therefore induces the droplet to split
3. coalescing two droplets into one by inducing a dipole moment by applying an electric field via adjacent electrodes connected to a voltage source or current source which mutually attracts the two droplets and transiently forms a bridge through which the fusing is initiated.
4. urging or moving a droplet by an electric force induced by an applied electric field in the direction of the channel, or at least having an electric field component in the direction of the channel. This may be used to direct a droplet down a particular leg of a bifurcation, for example to sort droplets with 2 or more distinct properties, or to route a droplet stream for a period of time.
5. removing charge from droplets (neutralizing) by moving the droplets past a ground electrode arranged closely adjacent the channel or in the channel Passive components may be fabricated from conductive patterning in which electric or magnetic fields are induced by the passage of droplets (inductive loop detector) The usual range of components known from radio frequency (RF) device fabrication may be used, including inductive, resistive and capacitive elements, and combinations thereof.

A simple passive component would be an electrode pair either side of a channel connected to form a sensing circuit including the channel, wherein the resistance would be affected, typically decreased, when a droplet passes the electrode pair Electrically conductive patterning may be used to fabricate electromagnetic sensors to integrate with the microfluidic device, such as a Hall sensor, which for example might be useful if the droplets were associated with magnetic beads. Another sensor type which can be used for sensing the passage of droplets is an antenna structure such as a bowtie antenna.

An electrode may extend substantially at right angles to the flow channel and terminate a small distance away from the flow channel edge, or at the flow channel edge, or in the flow channel, or may extend right through the flow channel. For example, a pair of electrodes can be provided both extending substantially at right angles to each other and terminating opposed to each other on either side of the flow channel.

Figure 2A:
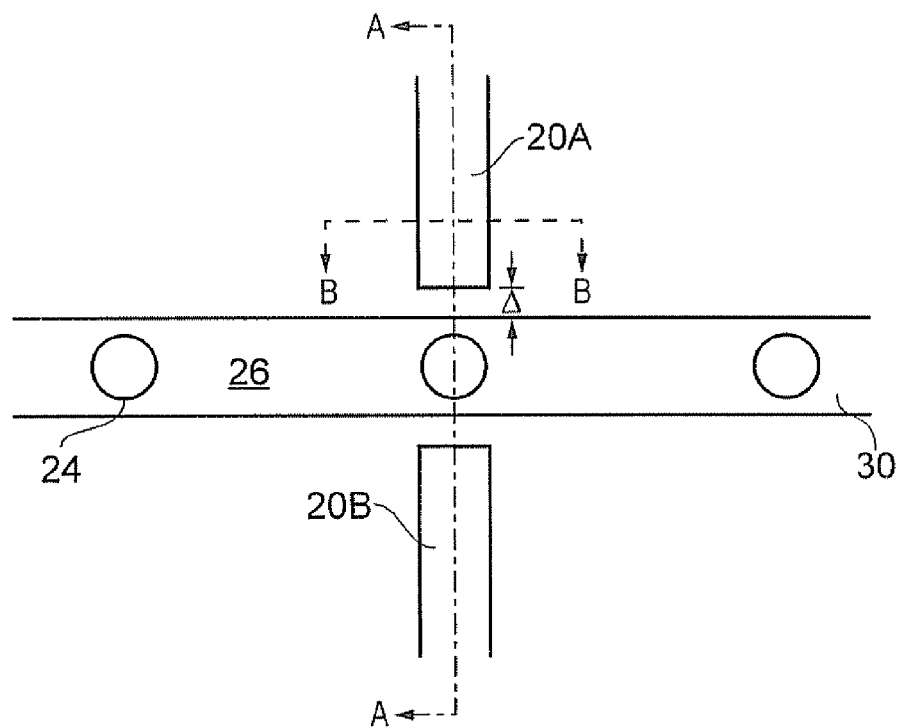
FIG. 2A is a plan view of a part of a microfluidic device incorporating a pair of electrodes manufactured as shown in FIG. 1F.
Figure 2B:
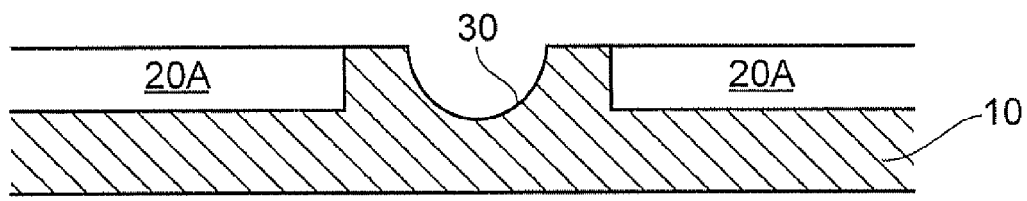
FIG. 2B is a section through line AA of FIG. 2A

Other electrodes may extend in the flow channel direction and either be located in the flow channel or adjacent the flow channel. For example, a pair of electrodes may be arranged to extend parallel to a channel on either side of the channel for a section of the channel so that an electric field may be applied transverse to the flow direction over the section of the flow channel A wide range of droplet diameter is also envisages including the nanometre range, in particular 100-1000 nanometres, as well as 1-1000 micrometres, in particular 1-100 micrometres The carrier liquid may be an oil The droplet liquid may be an aqueous solution, e.g. containing an enzyme, or an alcohol solution, or an oil solution FIG. 2A is a plan view of a part of a microfluidic device incorporating a pair of electrodes manufactured as shown in FIG. 1F A portion of a microfluidic flow channel 30 is shown in which the flow direction may be considered left to right in the drawing. The flow channel 30 is filled in use with a carrier liquid 26 in which is immiscibly suspended a series of droplets 24 of active liquid, e g of an analyte A first electrode channel 20A is arranged on one side of the flow channel and extends transverse to the flow channel and terminates a distance Δ from the adjacent rim or edge of the flow channel 30 A second electrode channel 20B is arranged on the other side of the flow channel co-linear with the first electrode channel 20A and also terminates a distance Δ from its adjacent rim or edge of the flow channel 30 The first and second electrode channels 20A, 20B arranged either side of the flow channel have conductive ink layers therein (not separately illustrated) which are formed in the manner described further above, and thereby form a pair of electrodes which can be externally actuated or sensed in order to control or sense the flow of the liquid droplets in the flow channel FIG. 2B is a section through the chain-dotted line AA of FIG. 2A from which the structure of the flow and electrode channels is evident.

Figure 2C:
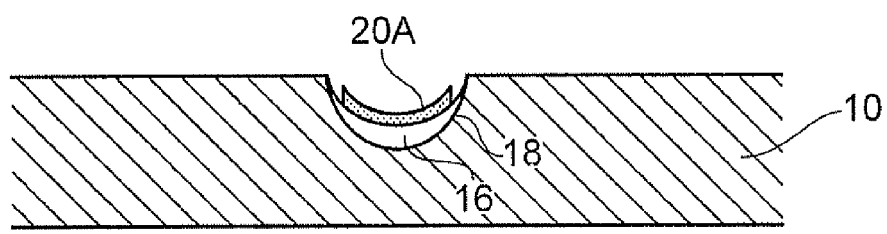
FIG. 2C is a section through line BB of FIG. 2A which is identical to FIG. 1F

FIG. 2C is a section through dotted line BB of FIG. 2A which is identical to FIG. 1F, i e shows the structure of the electrode channel with primer layer 16 and conductive ink layer 18

Figure 3:
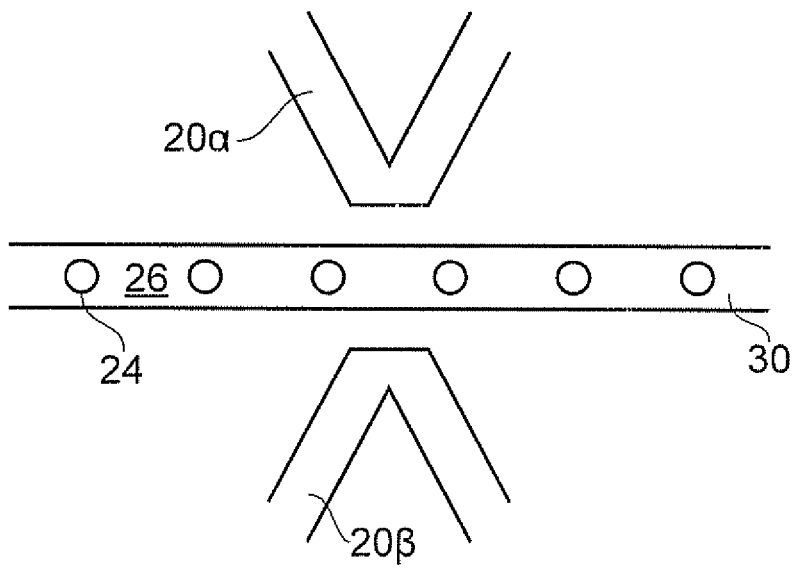
FIG. 3 is a plan view of a part of a microfluidic device incorporating a pair of electrodes having an alternative topography to that of FIG. 2A.

FIG. 3 is a plan view of a part of a microfluidic device incorporating a pair of electrodes having an alternative topography to that of FIG. 2A. The electrode channels $20\alpha$, $20\beta$ have a different shape than in the example of FIG. 2A. Namely, each electrode is formed in a continuous channel portion of V-shape with the base of the V being arranged adjacent the flow channel 30.

Figure 4:
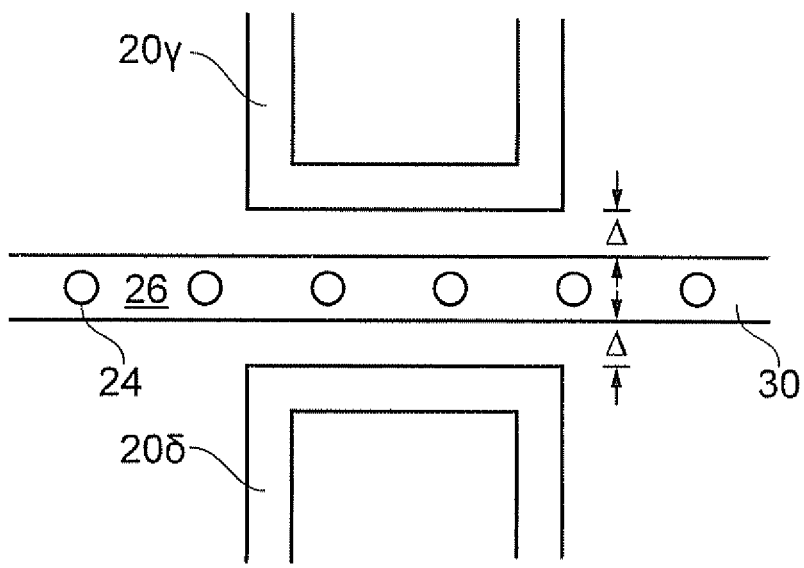
FIG. 4 is a plan view of a part of a microfluidic device incorporating a pair of electrodes having an alternative topography to that of FIG. 2A

FIG. 4 is a plan view of a part of a microfluidic device incorporating a pair of electrodes having another alternative topography. The electrodes on either side of the flow channel $20\gamma$, $20\delta$ are each formed from a continuous channel portion in a digital, i e flat-based, U-shape, so the part of the electrode that is adjacent the flow channel is defined by a portion of the electrode channel that extends parallel to the flow channel.

Figure 5:
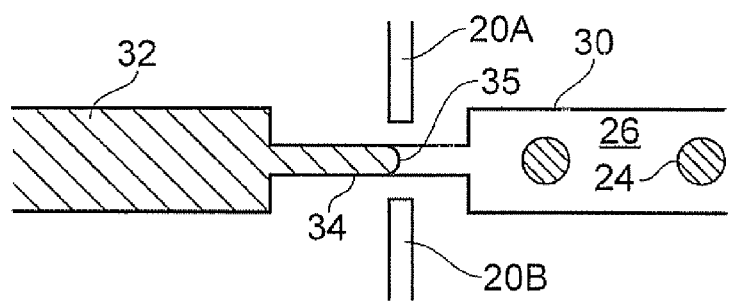
FIG. 5 is a schematic plan view of a component of a microfluidic device for generating droplets on demand.

Other continuous channel portion shapes may also be employed. Having the part of the electrode that is adjacent the flow channel formed by a continuous channel portion has the advantage during fabrication that more even capillary flow of the liquid primer and conductive ink will take place in the case that fabrication relies on capillary flow of either the primer or the conductive ink or both FIG. 5 is a schematic plan view of a component of a microfluidic device for generating droplets on demand A fluid reservoir 32 holds a volume of the active liquid (shaded) from which droplets 24 are formed. A pair of electrodes 20A, 20B are placed adjacent to a constricted channel portion 34 arranged between an outlet of the reservoir 32 and a flow channel 30. Absent actuation of the electrodes 20A, 20B the active liquid is in equilibrium with a meniscus 35 being formed in the constricted channel portion 34. When a voltage pulse is applied to the electrodes 20A, 20B, an electrophoretic force is applied to the portion of active liquid in the constricted channel portion 34, and a volume of the active liquid is broken off the contiguous reservoir volume and launched into the flow channel 30 as a droplet 24 Droplets may be produced on demand in this way, for example a series of droplets may be produced by repeatedly applying voltage pulses to the electrodes.

Figure 6:
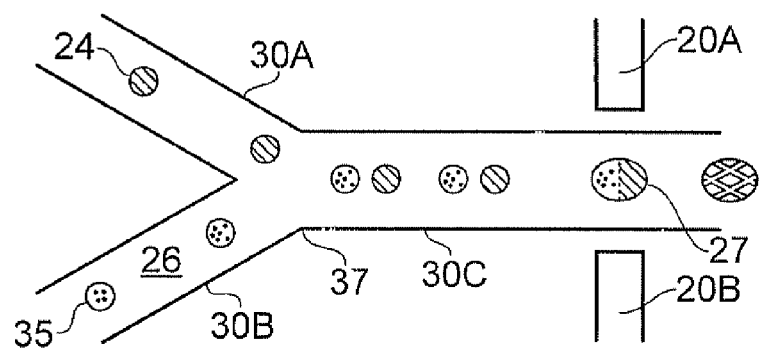
FIG. 6 is a schematic plan view of a component of a microfluidic device for coalescing pairs of droplets received from first and second channels.

FIG. 6 is a schematic plan view of a component of a microfluidic device for coalescing pairs of droplets received from first and second channels First and second inlet flow channels 30A and 30B combine as viewed in the direction of flow at a Y-junction 37 to form a single combined flow channel 30C. A series of droplets 24 of a first active liquid (shaded) are received from the first inlet flow channel 30A. A series of droplets 25 of a second active liquid (stippled) are received from the second inlet flow channel 30B The droplets 24, 25 are carried by a carrier liquid 26. The two series of droplets are controlled so that they arrive in adjacent pairs in the flow channel 300, i e with slightly offset arrival times, as illustrated An electrode pair 20A, 20B is arranged at a point in the flow of the flow channel 30C The electrodes are selectively actuated with a voltage pulse at times when droplet pairs 24, 25 pass by so as to cause each droplet pair to coalesce into a combined droplet 27 (cross-hatched) The mixture of the first and second liquids may serve to activate or deactivate a chemical reaction or a biological process depending on the application.

Figure 7:
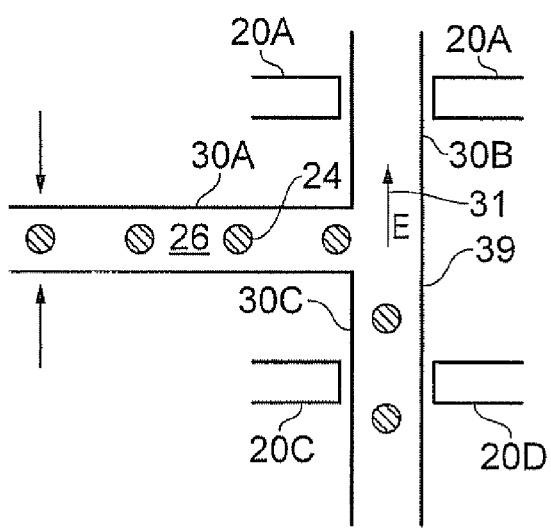
FIG. 7 is a schematic plan view of a component of a microfluidic device for routing or sorting droplets at a channel junction.
Figure 8:
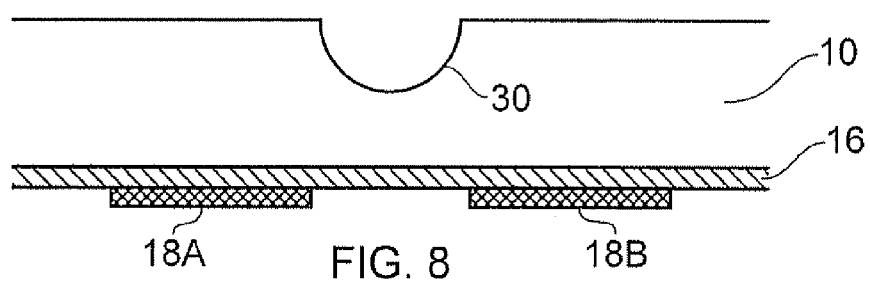
FIG. 8 is a schematic section of an alternative embodiment in which the electrodes are formed on the under side of the substrate

FIG. 7 is a schematic plan view of a component of a microfluidic device for routing or sorting droplets at a channel T-junction 39 A series of droplets 24 of an active liquid (shaded) carried in a carrier liquid 26 arrive along a flow channel 30A at the T-junction 39 at which the flow splits into a left flow channel 30B and a right flow channel 30C. A left electrode pair 20A, 20B is arranged part way along the left flow channel 30B and a right electrode pair 20C, 20D is arranged part way along the right flow channel 30C The left and right electrode pairs are operated in tandem to apply an electric field either in the direction shown with the arrow 31 or the opposite direction in order to route the droplets 24 arriving along channel 30A down the left channel 306 or the right channel 30C (as illustrated) Additionally if the routing function was to be modified to be a sorting function, a sensor 38 can be arranged in the flow upstream of the T-junction, as schematically illustrated, to measure a property of each droplet on the basis of which sorting is to be performed. Individual droplets may then be directed down the left or right flow channels 30B, 30C depending on their measured properties The sensor 38 could be an electromagnetic sensor formed with conductive ink elements made according to the method described herein, or could be an unrelated type of sensor, such as a sensor operable to make an image-based measurement (i e camera or microscope with image processing) or a spectroscopic measurement FIG. 8 is a schematic section of an alternative embodiment in which the electrodes are formed on the under side of the substrate. The embodiment is based on the same kind of substrate as the previously illustrated embodiments, i.e a planar structure 10 with flow channels 30 of semi-circular cross-section arranged on an upper surface 12 thereof. In this embodiment, the primer layer 16 and conductive ink electrodes 18A and 18B are not arranged in a channel formed on the substrate's upper surface 12. Instead, the conductive ink electrodes 18A, 18B are arranged in corresponding locations in plan view as illustrated in FIG. 2A, but on the underside, i e lower surface 14, of the substrate 10 The primer layer 16 is formed, as illustrated, as a blanket layer covering the whole of the substrate's lower surface 14, or at least an area that does not closely follow the conductive ink pattern Alternatively, the primer layer 16 could be restricted to follow the area of the conductive ink pattern, with margin regions in some embodiments provided to avoid problems from registration errors between the primer and ink deposition steps following a general approach commonly used in semiconductor photolithography It will be understood that further embodiments may combine the previously discussed embodiments and include conductive ink patterning on both sides of the substrate. For example, some components, such as antennas or surface RF components such as RLC components, may be beneficially fabricated on a planar surface, i.e. typically the substrate's lower surface 14, whereas electrodes that extend into the flow channels to form conductive paths including liquid in the flow channels will need to be fabricated on the substrate's upper surface 12 where the flow channels exist

EXAMPLES

Figure 9A:
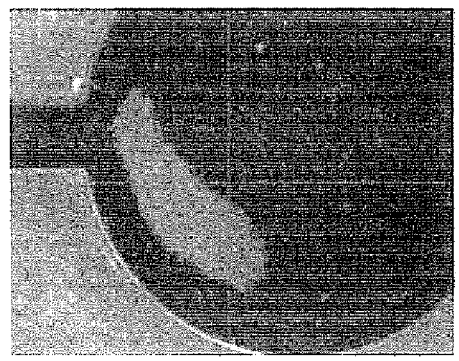
FIG. 9A is a photograph showing results of electrode printing into a channel without pre-treating the substrate with the example primer

FIG. 9A is a photograph showing results of electrode printing into a channel of a cycloolefin polymer (COP) substrate in the case that the substrate was not treated with the example primer before printing Uneven coverage of ink is evident including a large kidney-shaped region in which no ink has remained.

Figure 9B:
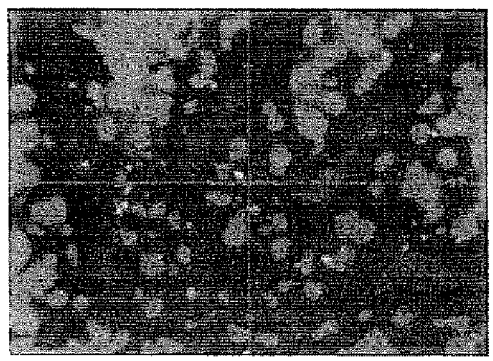
FIG. 9B is a photograph showing results of electrode printing onto an unstructured surface without pre-treating the substrate with the example primer.
Figure 9C:
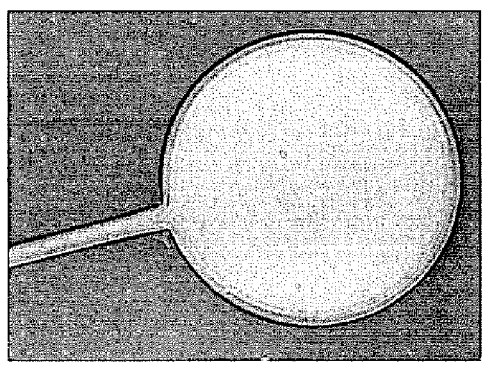
FIG. 9C is a photograph to be compared with FIG. 9A showing results of electrode printing into a channel after pre-treating the substrate with the example primer.
Figure 9D:
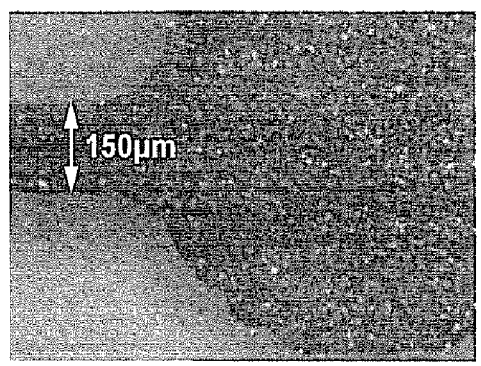
FIG. 9D is a photograph to be compared with FIG. 9C showing results of electrode printing onto an unstructured surface after pre-treating the substrate with the example primer
Figure 10:
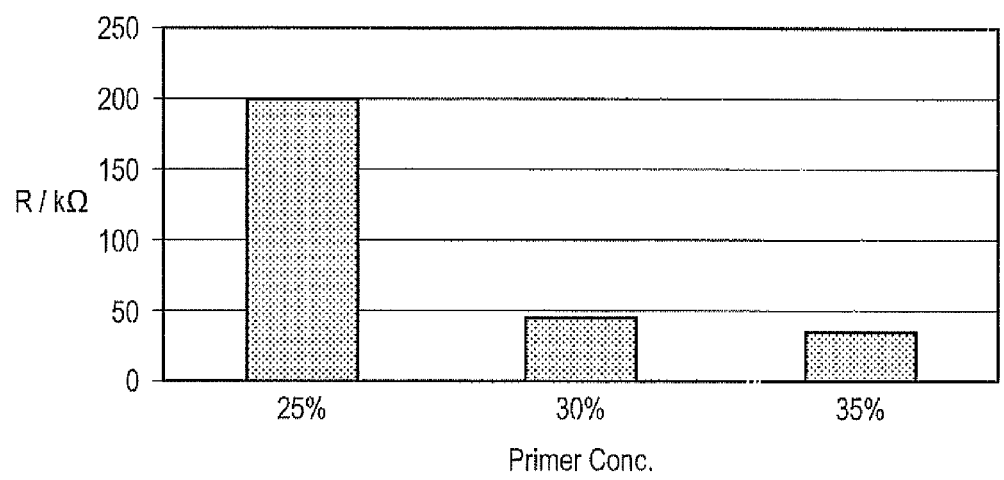
FIG. 10 is a bar chart showing average resistance of a conductive layer according to three batches of samples.

FIG. 9B is a photograph showing results of electrode printing onto an unstructured glass surface without pre-treating the substrate with the example primer. Uneven coverage of ink is evident including many voids which seem to have been formed from approximately circular voids some of which have merged to form larger void regions FIG. 9C is a photograph to be compared with FIG. 9A showing results of electrode printing into a channel of a COP substrate after pre-treating the substrate with the example primer A relatively uniform ink coverage is evident with no voids FIG. 9D is a photograph to be compared with FIG. 9C showing results of electrode printing onto an unstructured glass surface after pre-treating the glass substrate with the example primer A relatively uniform ink coverage is evident with no voids FIG. 10 is a bar chart showing average resistance of a conductive ink layer, which was based on Ag The primer layer was applied by syringe dispensing into the channels. Sintering was carried out for 30 minutes at a temperature of 80° C. Results are shown for batches of samples at three different primer concentrations of 25%, 30% and 35%, the concentration being of the primer concentrate (organic polymer and porous particulate material) in the glycol ether solvent.

Without a primer layer, the Ag ink layer had resistances in the range 100 to 500 kΩ With the 25% primer layer, the Ag ink layer had an average resistance of 200Ω With the 30% primer layer, the Ag ink layer had an average resistance of approximately 45Ω With the 35% primer layer, the Ag ink layer had an average resistance of approximately 35Ω. Increasing concentrations of primer concentrate in the primer layer therefore result in an increasingly conductive Ag ink layer being deposited. The concentration of primer concentrate in the primer layer can therefore be used to control the resistivity of the conductive ink layer which is an important parameter to have control over, especially when the conductive patterning is used as part of an electronic circuit, i.e. is more than simply a contact electrode.

What is not shown in the figure, which is also important, is that the range of resistances within each of the three batches was much smaller than the range of resistances of the control batch where no primer was used As stated above, without a primer layer, the Ag ink layer had resistances in the range 100 to 500 kΩ, i.e. a nominal average of 300 kΩ±200 kΩ. For the 25% concentration batch, the resistance was 200 Ω±~50 kΩ. For the 30% concentration batch, the resistance was 45Ω±~10Ω. For the 35% concentration batch, the resistance was 35Ω±~5Ω. With reference to FIGS. 9A to 9D, these results are attributed to the use of the primer providing a more even distribution of the ink and an improved conductive metallic layer.

Example 1

Polymer Comparison

Method

A series of polymers were selected and subjected to microfluidic flow tests The polymers tested were as follows (polymers 5 and 6 are polymers according to the present invention, polymers 1 to 4 are comparative examples):

1 Induquat™ ECR 956 L, a cationic polyacrylate designed for transparent ink et receptive coatings, available from Indulor Chemie GmbH.

2 CAP 482-0,5, a cellulose acetate propionate with extensive solubility in glycol ethers, available from Eastman Chemical Co.

3. CAB 553-0,4, a cellulose acetate butyrate with extensive solubility in glycol ethers, available from Eastman Chemical Co 4. Neocryl™ B890, a modified methyl methacrylate/butyl methacrylate copolymer with extensive solubility in glycol ethers, available from DSM NeoResins.

Figure 11:
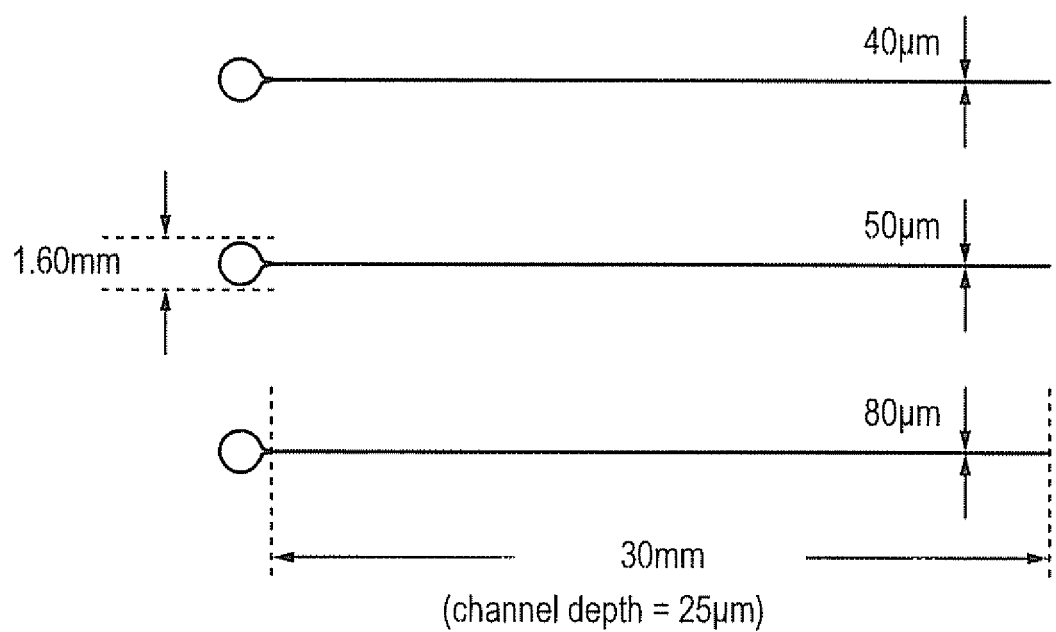
FIG. 11 is a schematic of an electrode test channel in a cycloolefin polymer moulded chip

5 PVP K90™, a polyvinyl pyrrolidone homopolymer with extensive solubility in glycol ethers, available from ISP Inc.
6. Copolymer 958, a vinyl pyrrolidone/dimethylaminoethyl-methacrylate copolymer with extensive solubility in glycol ethers, available from ISP Inc Initially, solutions of the polymers were prepared at 10% by weight concentration in ethanol These ethanol-based solutions were then further diluted in a ratio of 1:4 and 2:3 polymer solution with isopropoxyethanol or dipropylene glycol monomethyl ether A volume of 2 µl of the diluted polymer solution was dispended in the pad area on the electrode test pattern moulded in COP depicted in FIG. 11. The flow of the polymer solutions was gauged visually under magnification and comments recorded. The results are shown in Table 1 below

TABLE 1

| Polymer | 1.4 isopropoxy-ethanol | 2:3 isopropoxy-ethanol | 1:4 dipropylene glycol mono-methyl ether | 2.3 dipropylene glycol mono-methyl ether |
|---|---|---|---|---|
| 1 ECR 956L | OF | IF | OF | IF |
| 2 CAP 482-0.5 | OF | IF | OF | IF |
| 3 CAB 553-0.4 | OF | IF | OF | IF |
| 4 Neocryl B890 | OF | IF | OF | GF |
| 5 PVP K90 | GF | IF | GF | IF |
| 6 Copolymer 958 | GF | IF | GF | GF |

Key:
OF = overflowing out of channels (undesired)
IF = insufficient flowing in channels, non-uniform coverage
GF = good flowing in channels, defect-free and uniform coverage Good flowing in the microfluidic channels was only seen for the polymer samples Neocryl B890, PVP K90 and Copolymer 958, Copolymer 958 affording the best overall result Example 2

Solvent Comparison

Method
A primer concentrate was made according to the present invention using the following method:
Copolymer 958 ex ISP supplied as 50% by weight in ethanol was diluted to 10% concentration by stirring in additional ethanol. The porous particle alumina boehmite (Dispel® 14N4-80, available from Sasol GmbH) is supplied in powder form.
A dispersion of Dispel® 14N4-80 at 10% concentration by weight in water was made on a high speed stirrer, adjusting the pH to 3-5 with glacial acetic acid to ensure a low pH environment and hence a uniform dispersion. The two preparations, both at 10% concentration by weight, were blended together in a ratio of 4 parts by weight of the Dispel® 14N4-80 dispersion to 1 part by weight of the Copolymer 958 solution The resulting preparation is designated as "Primer Concentrate 1"
Primer concentrate 1 was further diluted with a series of solvents, also in a weight ratio of 1:4 (concentrate:solvent) and a volume of 2 µl was dispended in the pad area on the electrode test pattern moulded in COP described above. The flow of the primer in the test channels was gauged in terms of flow rate and total distance flowed in each channel.

The results are shown in Table 2 below In each case, the concentrate (Primer concentrate 1) was diluted in a ratio of concentrate (1 part):solvent (4 parts)

TABLE 2

| Solvent | Flow Rate (Relative Scale) | Flow Distance (100% = 30 mm) |
|---|---|---|
| Deionised water | 0 | no |
| Isopropanol | 4 | 30% |
| Ethanol | 5 | 30% |
| Methoxyisopropanol | 3 | 35-40% |
| Isopropoxyethanol | 4 | 60-70% |
| Dipropylene glycol monomethyl ether | 4 | 100% |
| N-methyl pyrrolidone | 0 | no |

Clearly, the concentrate diluted with the glycol ether solvents exhibited the best flow of the primer in the test channels on the fluidic chip. Furthermore, the glycol ether containing samples showed no sign of overflow from the fluidic test channels Example 3

Comparison of Porous Particles in Functional Primer

Method and Results
A microfluidic test pattern as depicted in FIG. 1 with circular pads at both ends of the channels, and the primer described in Example 2 diluted with dipropylene glycol monomethyl ether, was used to compare the effect of the type of porous particle in the performance of the primer layer After ink jet printing a silver nanoparticle based ink on to the dried primer layer, the relative performance of the primer was judged by measuring the resultant electrical resistance of the completely filled electrode pattern The printed silver ink was dried at 80° C. for 30 minutes before taking electrical measurements Example 3a Primer concentrate 1 was made according to Example 2 and diluted 1 part to 4 parts by weight with dipropoylene glycol monomethyl ether. The dispensed primer in the microfluidic test channels was dried at 80° C. for 2 minutes before over-printing with SunTronic™ U5603 silver ink (available from Sun Chemical) The pore volume of the Dispel® 14N4-80 used in this example is 0 50 ml/g.
The electrical resistance of the test channels after printing/drying of ink ranged from 250 to 300Ω It was noted the test channel was completely and uniformly covered with both the primer and subsequently printed ink.

Example 3b

Primer concentrate 1 was made according to Example 2 and diluted 1 part to 4 parts by weight with dipropylene glycol monomethyl ether wherein the Dispal® 14N4-80 was directly replaced by alumina (Dispal® 18N4-80, pore volume 0.50 ml/g) on a weight for weight basis. The dispensed primer in the microfluidic test channels was dried at 80° C. for 2 minutes before over-printing with SunTronic™ U5603 silver ink (available from Sun Chemical).
The electrical resistance of the test channels after printing/drying of ink ranged from 250 to 300Ω It was noted the test channel was completely and uniformly covered with both the primer and subsequently printed ink.

Example 3c

Primer concentrate 1 was made according to Example 2 and diluted 1 part to 4 parts by weight with dipropylene glycol monomethyl ether wherein the Dispal® 14N4-80 was directly replaced by silica (Syloid™ C809, available from Grace Davison; pore volume 2 0 ml/g) on a weight for weight basis The dispensed primer in the microfluidic test channels was dried at 80° C. for 2 minutes before over-printing with SunTronic™ U5603 silver ink (available from Sun Chemical).

The electrical resistance of the test channels after printing/drying of ink ranged from 800 to 850Ω It was noted the test channel was not completely and uniformly covered with both the primer and subsequently printed ink.

Example 3d

Primer concentrate 1 was made according to Example 2 and diluted 1 part to 4 parts by weight with dipropylene glycol monomethyl ether wherein the Dispal 14N4-80 was directly replaced by Syloid™ W300 (pore volume 1 20 ml/g) on a dry weight for weight basis The dispensed primer in the microfluidic test channels was dried at 80° C. for 2 minutes before over-printing with SunTronic™ U5603 silver ink (available from Sun Chemical)

The electrical resistance of the test channels after printing/drying of ink ranged from 650 to 700Ω. It was noted the test channel was not completely and uniformly covered with the primer leading to voids in the printed ink A reference example was also carried out, omitting a porous particulate matter, and including only the polymer, yielded an electrical resistance of 1 to 1.5 kΩ

All publications mentioned in the above specification are herein incorporated by reference Various modifications and variations of the described methods and system of the present invention will be apparent to those skilled in the art without departing from the scope and spirit of the present invention Although the present invention has been described in connection with specific preferred embodiments, it should be understood that the invention as claimed should not be unduly limited to such specific embodiments Indeed, various modifications of the described modes for carrying out the invention which are obvious to those skilled in chemistry, physics and materials science or related fields are intended to be within the scope of the following claims.

What is claimed is:

1. A microfluidic device, comprising:
  a substrate comprising a microfluidic channel; and
  an electrically conductive feature comprising an electrically conductive layer arranged on a primer layer and positioned with reference to the microfluidic channel, wherein the primer layer comprises:
  (i) an organic polymer selected from the group consisting of
    (a) a homopolymer or copolymer comprising a vinyl lactam repeating unit,
    (b) a cellulose ether,
    (c) polyvinyl alcohol, and
    (d) unmodified or modified gelatin, and
  (ii) a porous particulate material,
  wherein the porous particulate material is dispersed in the organic polymer, and
  wherein the microfluidic channel comprises a side wall portion that joins an upper surface of the substrate at a rim and a lateral separation δ exists between the rim of the microfluidic channel and the edge of the electrically conductive layer.

2. The microfluidic device of claim 1, wherein the primer layer comprises at least 70% by weight of the porous particulate material, based on a total weight of the organic polymer and porous particulate material.

3. The microfluidic device of claim 2, wherein the primer layer comprises up to 30% by weight of the organic polymer, based on a total weight of the organic polymer and porous particulate material.

4. The microfluidic device of claim 1, wherein the primer layer comprises at least 90% by weight of the porous particulate material, based on a total weight of the organic polymer and porous particulate material.

5. The microfluidic device of claim 4, wherein the primer layer comprises up to 10% by weight of the organic polymer, based on a total weight of the organic polymer and porous particulate material.

6. A method of manufacturing a microfluidic device, the method comprising:
  (A) applying a primer layer to a substrate comprising a microfluidic channel, the primer layer comprising:
    (i) an organic polymer selected from the group consisting of
      (a) a homopolymer or copolymer comprising a vinyl lactam repeating unit,
      (b) a cellulose ether,
      (c) polyvinyl alcohol, and
      (d) unmodified or modified gelatin, and
    (ii) a porous particulate material, wherein the porous particulate material is dispersed in the organic polymer;
  (B) applying a conductive ink layer over the primer layer at a position referenced to the microfluidic channel, the conductive ink comprising electrically conductive particles dispersed in a humectant organic solvent,
  wherein during (A) applying the primer layer and/or (B) applying the conductive ink layer, the primer layer and/or the conductive ink layer are applied to the microfluidic channel, and
  wherein the microfluidic channel comprises a side wall portion that joins an upper surface of the substrate at a rim and the conductive ink layer is applied in the microfluidic channel so that a lateral separation δ exists between the rim of the conductive ink channel and the edge of the conductive ink layer.

7. The method according to claim 6, wherein, during (A) applying the primer layer and/or (B) applying the conductive ink layer, the primer layer and/or the conductive ink layer are applied in solution to the microfluidic channel and are distributed through the microfluidic channel by capillary action.

8. The method according to claim 6, wherein the organic polymer is a homopolymer or copolymer of vinyl pyrrolidone.

9. The method according to claim 8, wherein the organic polymer is a copolymer of vinyl pyrrolidone and dimethylaminoethylmethacrylate.

10. The method according to claim 6, wherein the porous particulate material is selected from the group consisting of silica, alumina, titania, a zeolite, and barium sulphate.

11. The method according to claim 6, wherein the primer layer is applied to the substrate diluted in a hydrophilic solvent.

12. The method according to claim 11, wherein the hydrophilic solvent is a glycol ether or a mixture thereof.

13. The method according to claim 6, wherein the electrically conductive particles in the conductive ink comprise a metal selected from the group consisting of nickel, copper, palladium, silver, platinum and gold, or any mixture thereof.

14. The method according to claim 6, wherein the humectant organic solvent in the conductive ink is a polyol.

15. A microfluidic device manufactured according to the method of claim 6.

* * * * *